United States Patent
Kralisch et al.

(10) Patent No.: US 11,859,227 B2
(45) Date of Patent: Jan. 2, 2024

(54) METHOD FOR PRODUCING BACTERIALLY SYNTHESIZED CELLULOSE NON-WOVEN

(71) Applicant: JENACELL GMBH, Jena (DE)

(72) Inventors: Dana Kralisch, Jena (DE); Elena Pfaff, Jena (DE); Daniela Rossner, Jena (DE)

(73) Assignee: JENACELL GMBH, Jena (DE)

( * ) Notice: Subject to any disclaimer, the term of this patent is extended or adjusted under 35 U.S.C. 154(b) by 747 days.

(21) Appl. No.: 16/615,656

(22) PCT Filed: May 24, 2018

(86) PCT No.: PCT/EP2018/063664
§ 371 (c)(1),
(2) Date: Nov. 21, 2019

(87) PCT Pub. No.: WO2018/215598
PCT Pub. Date: Nov. 29, 2018

(65) Prior Publication Data
US 2020/0208185 A1   Jul. 2, 2020

(30) Foreign Application Priority Data

May 24, 2017 (EP) .................... 17172847

(51) Int. Cl.
| | |
|---|---|
| *C12P 19/04* | (2006.01) |
| *C12M 1/00* | (2006.01) |
| *C12M 1/34* | (2006.01) |
| *D04H 3/013* | (2012.01) |

(52) U.S. Cl.
CPC ............. *C12P 19/04* (2013.01); *C12M 29/00* (2013.01); *C12M 41/12* (2013.01); *D04H 3/013* (2013.01)

(58) Field of Classification Search
CPC ......... C12P 19/04; C12M 29/00; C12M 41/12
See application file for complete search history.

(56) References Cited

FOREIGN PATENT DOCUMENTS

| | | |
|---|---|---|
| DE | 10 2007 010 866 | 9/2008 |
| DE | 10 2013 001 002 | 7/2014 |
| EP | 0 323 717 | 7/1989 |
| KR | 10-2014-0129234 | 11/2014 |
| WO | 2010/028632 | 3/2010 |
| WO | 2010/029044 | 3/2010 |

OTHER PUBLICATIONS

Kondo T et al. Aqueous counter collision using paired water jets as a novel means of preparing nano-fibers. 2014. Carbohydrate Polymers. 112:284-290. (Year: 2014).*
Silindir M et al. Sterilization Methods and the Comparison of E-Beam Sterilization with Gamma Radiation Sterilization. 2009. FABAD J. Pharm. Sci. 34, 43-53. (Year: 2009).*
International Search Report and Written Opinion of the International Searching Authority, dated Jul. 16, 2018 in corresponding International Patent Application No. PCT/EP2018/063664.
Extended European Search Report, dated Nov. 6, 2017 in corresponding European Patent Application No. 17172847.0.
Sulaeva et al., "Bacterial cellulose as a material for wound treatment: Properties and modifications. A review", Biotechnology Advances, 33(8): 1547-1571 (2015).
Office Action dated Feb. 27, 2023 in corresponding Chinese Patent Application No. 201880034622.2, with English language translation.
Tetsuo Kondo et al., "Aqueous counter collision using paired water jets as a novel means of preparing bio-nanofibers", Carbohydrate Polymers, vol. 112, pp. 284-290, 2014.
English translation of Office Action dated May 25, 2023 in Korean Application No. 10-2019-7038141.

* cited by examiner

*Primary Examiner* — Paul J Holland
(74) *Attorney, Agent, or Firm* — Wenderoth, Lind & Ponack, L.L.P.

(57) ABSTRACT

The present invention relates to a method for producing bacterially synthesized cellulose (BC) non-woven as well as to BC non-woven produced by the method and uses of such BC non-woven. The present invention also relates to an apparatus for production of the BC non-woven. Preferably, the bacterially synthesized cellulose (BC) of the present invention is biotechnologically produced nano-structured cellulose (BNC).

16 Claims, 2 Drawing Sheets

METHOD FOR PRODUCING BACTERIALLY SYNTHESIZED CELLULOSE NON-WOVEN

The present invention relates to a method for producing biotechnologically produced cellulose (BC) non-woven as well as to BC non-woven produced by the method and uses of such BC non-woven. The present invention also relates to an apparatus for production of the BC non-woven. Preferably, the bacterially synthesized cellulose (BC) of the present invention is biotechnologically produced nano-structured cellulose (BNC). The terms "biotechnologically produced cellulose" and "bacterially synthesized cellulose" are used interchangeably in the present specification.

The present invention relates to BC. BC is an extracellular polysaccharide produced by different bacteria, including *Komagatagaibacter, Agrobacter* and *Sarcina* strains. BC is a cellulose that may be nanostructured. Nanostructured BC is termed BNC (bacterially synthesized nanostructured cellulose). In comparison to conventional cellulose, BC is characterized by several advantageous properties. In particular, it has a high tensile strength, flexibility, and water holding capacity, a pronounced permeability to gases and liquids, and a great compatibility with living tissues (Sulaeva, I., Henniges, U., Rosenau, T., Potthast, A., 2015. Bacterial cellulose as a material for wound treatment: Properties and modifications. A review. Biotechnology Advances 33, 1547-1571). The method of the present invention enables production of BC non-woven. According to the present invention, a BC non-woven is in particular a non-woven of fibers of BC. The terms "BC non-woven" and "BC fleece" may be used interchangeably in accordance with the present invention.

Methods for producing bacterial cellulose are known in the art. Particularly, static or discontinuous production processes, like static fermentation, are used. Most of the BC that is produced today is produced by fermentation of coconut water in a static batch process ("nata de coco"). However, BC produced by the known static or discontinuous production processes is relatively expensive, and comes along with various drawbacks, particularly with disadvantageous or at least sub-optimal properties of the produced bacterial cellulose. Moreover, in static manufacturing processes the production of bacterial BC is limited by the batch-wise production. For example, documents CN 101386877 A, CN 102784071 A and U.S. Pat. No. 4,655,758 A disclose production of BC in static processes. The bacterial cellulose produced in such prior art processes is of relatively high density and possesses a low tensile strength. Due to the relatively low tensile strength, BC articles of the prior art also easily tear.

Also methods for semi-static production of BC non-woven have been described before. For example, WO 2010/028632 A2 describes a method for producing BC in planar form. BC non-woven is produced in a culture vessel and finished BC non-woven is removed. Non-finished BC non-woven remains in the culture vessel until the BC non-woven has reached the desired thickness. WO 2010/028632 A2 discloses a cultivation temperature of from 20° C. to 32° C. and an air supply of from 1 to 200 l/min.

In principle, semi-static production of BC non-woven may be step-wise or continuous. In other words, removal of BC from the culture vessel may be done step-wise or continuously. Yield of BC non-woven is comparably low with the prior art methods. WO 2010/028632 A2 discloses that BC non-woven of 0.5 to 1.6 cm thickness is obtained only after 10 to 16 days of incubation.

Moreover, the prior art methods have the drawback that the BC non-woven that is obtained comprises a substantial amount of BC pre-polymer. Such pre-polymer has to be removed before the BC non-woven can be used. The BC pre-polymer basically consists of a very loose network of fibers and thus represents a precursor of the finished BC non-woven. In the prior art methods, the efficiency of BC production is comparably low. Thus, the produced pre-polymer may descend away from the interface with air deeper into the culture medium before production of the finished BC non-woven is completed. However, deeper inside the culture medium there are relatively low levels of oxygen as compared to the interface with air. Consequently, further production of BC will substantially halt in the descended parts so that the material will not reach the finished BC non-woven state but will instead remain in the pre-polymer state. Due to its inferior mechanical properties, the loose pre-polymer is disadvantageous for most kind of application and has thus to be removed in an additional process step. It would therefore be highly advantageous if the efficiency of BC non-woven production was increased in such a way that conversion from the pre-polymer state to the finished BC non-woven state was substantially completed prior to descent of the material away from the interface with air deeper into the culture medium.

Optionally, the terms "pre-polymer" or "pre-polymer material" as used in the present specification refer to a gelatinous cellulose layer on the bottom of BC non-woven characterized by a looser BC network compared to that of the surface or middle layer.

It is an object of the present invention to solve the problem of the prior art and to provide a method with increased yield of BC non-woven and increased efficiency of production. It is also an object of the present invention to provide a method for producing BC non-woven, wherein the consumption of culture medium is particularly low.

Furthermore, it is an object of the present invention to provide accordingly produced BC non-woven, in particular BC non-woven with excellent tensile strength, in particular BC non-woven having improved specific tensile strength, wherein specific tensile strength indicates the tensile strength of a BC non-woven divided by the thickness of the BC non-woven. It is also an object of the present invention to provide BC non-woven with particularly homogeneous network structure, in particular very homogeneous density of the network structure, and with particularly homogeneous surface structure.

Moreover, it is also an object of the present invention to provide uses of such BC non-woven.

It also an object of the present invention to provide an apparatus for the production of the BC non-woven.

The problem is solved by the subject-matter of the patent claims. The problem is in particular solved by a method for producing BC non-woven comprising the steps of a) Synthesizing BC by incubating a bacterial culture in a culture vessel, wherein the bacterial culture comprises liquid culture medium and BC-synthesizing bacteria, b) Optionally adding fresh or recycled culture medium and/or removing consumed culture medium during the incubation, c) Removing produced BC non-woven having an average thickness of at least 0.5 mm from the culture vessel.

Preferably, at least during step a), more preferably at least during steps a) and b), more preferably during steps a) to c) the gaseous atmosphere above the bacterial culture is kept at a temperature that is at most 10 K below the highest temperature of the culture medium in the culture vessel within a distance from the interface of BC and gaseous atmosphere of from 0 to 2 cm measured perpendicular to the interface. This means that the temperature condition is met throughout the mentioned distance from the interface, i.e. at all distances within the range of from 0 to 2 cm. Generally, the temperature decrease with increasing distance from the interface.

None of the prior art methods discloses that the temperature of the air above the bacterial culture is controlled and should be similar to the temperature of the culture medium in the culture vessel, at least within a certain distance from the interface of BC and air.

The present inventors found that it is advantageous if the gaseous atmosphere above the bacterial culture is kept at a temperature that is at most 10 K below the highest temperature of the culture medium in the culture vessel within a distance from the interface of BC and gaseous atmosphere of from 0 to 2 cm measured perpendicular to the interface. In particular, BC non-woven can be obtained with increased space-time-yield. In other words, BC non-woven with good tensile strength can be obtained after comparably short production times as compared to the prior art. Moreover, in particularly preferred embodiments the amount of remaining BC pre-polymer bound to the BC non-woven may be drastically reduced because the efficiency of BC non-woven production may be increased in such a way that conversion from the pre-polymer state to the finished BC non-woven state may be substantially completed prior to descent of the material away from the interface with air deeper into the culture medium. Preferably, finished BC non-woven of the present invention does not contain more than 20% by weight, more preferably not more than 10% by weight of loose pre-polymer material.

As described above, the temperature control of the present invention is advantageous in static BC production. However, the present inventors found that even better results can be achieved if the inventive temperature control is utilized in step-wise or continuous semi-static methods. Therefore, preferably synthesis of BC in the culture vessel continues during removal of BC non-woven having an average thickness of at least 0.5 mm from the culture vessel according to step c) of the method, wherein non-finished BC non-woven remains in the culture vessel and is separated from the BC non-woven that is removed, wherein the method preferably comprises the following steps:

d) Continuation of synthesis of BC in the culture vessel by continuation of incubation of the bacterial culture in the culture vessel, e) Optionally adding fresh or recycled culture medium and/or removing consumed culture medium during the continued incubation, f) Removing produced BC non-woven having an average thickness of at least 0.5 mm from the culture vessel, wherein synthesis of BC optionally continues during removal and wherein optionally non-finished BC non-woven remains in the culture vessel and is separated from the BC non-woven that is removed, and g) Optionally repeating steps d) to f) at least once, Preferably, at least during steps a) and d), more preferably at least during steps a), b), d) and e), more preferably during steps a) to g) the gaseous atmosphere above the bacterial culture is kept at a temperature that is at most 10 K below the highest temperature of the culture medium in the culture vessel within a distance from the interface of BNC and gaseous atmosphere of from 0 to 2 cm measured perpendicular to the interface.

According to the present invention, a temperature of the gaseous atmosphere of "at most X K" below the highest temperature of the culture medium indicates that the temperature of the gaseous atmosphere is not lower than the indicated lower limit. However, this does not mean that the temperature of the gaseous atmosphere is necessarily lower than the temperature of the culture medium. Rather, the temperature of the gaseous atmosphere and the temperature of the culture medium may also be substantially equal or the temperature of the gaseous atmosphere may even be higher than the temperature of the culture medium. In embodiments, the temperature of the gaseous atmosphere is not higher than the temperature of the culture medium.

Preferably, the gaseous atmosphere above the bacterial culture is kept at a temperature that is at most 5 K, more preferably at most 4 K, more preferably at most 3 K, more preferably at most 2 K, more preferably at most 1 K, more preferably at most 0.5 K, more preferably at most 0.1 K below the highest temperature of the culture medium in the culture vessel within a distance from the interface of BC and gaseous atmosphere of from 0 to 2 cm measured perpendicular to the interface. In particularly preferred embodiments, the gaseous atmosphere above the bacterial culture is kept at a temperature that is at least as high as the temperature of the culture medium in the culture vessel within a distance from the interface of BC and gaseous atmosphere of from 0 to 2 cm measured perpendicular to the interface. Preferably, the gaseous atmosphere above the bacterial culture is kept at a temperature that is at most 10 K, more preferably at most 5 K, more preferably at most 4 K, more preferably at most 3 K, more preferably at most 2 K, more preferably at most 1 K, more preferably at most 0.5 K, more preferably at most 0.1 K above the highest temperature of the culture medium in the culture vessel within a distance from the interface of BC and gaseous atmosphere of from 0 to 2 cm measured perpendicular to the interface. Preferably, the gaseous atmosphere above the bacterial culture is kept at a temperature of at most ±10 K, more preferably at most ±5 K, more preferably at most ±4 K, more preferably at most ±3 K, more preferably at most ±2 K, more preferably at most ±1 K, more preferably at most ±0.5 K, more preferably at most ±0.1 K as compared to the temperature of the culture medium in the culture vessel within a distance from the interface of BC and gaseous atmosphere of from 0 to 2 cm measured perpendicular to the interface.

As described above, a low temperature difference between culture medium and gaseous atmosphere is connected to an increased space-time-yield. Furthermore, a low temperature difference between culture medium and gaseous atmosphere is connected to production of BC non-woven with particularly high tensile strength, in particular BC non-woven having improved specific tensile strength, wherein specific tensile strength indicates the tensile strength of a BC non-woven divided by the thickness of the BC non-woven. A low temperature difference between culture medium and gaseous atmosphere is also connected to production of BC non-woven with particularly homogeneous network structure, in particular very homogeneous density of the network structure, and with particularly homogeneous surface structure.

Moreover, a low temperature difference between culture medium and gaseous atmosphere is also advantageous for another reason. In particular, in embodiments in which the culture vessel is covered with a cover, a low temperature difference between culture medium and gaseous atmosphere results in very little or even substantially no condensation of liquid on the surfaces of the cover or other surfaces that face the interior of the culture vessel. It is preferable to reduce or even avoid such condensation because otherwise liquid drops might fall from the surface of the cover into the culture vessel and may thereby disturb BC production and deteriorate quality of the produced BC non-woven. Moreover, in certain embodiments of the present invention the cover covering the culture vessel may be transparent in order to enable online visual inspection and/or optical analysis of the production process, preferably using imaging techniques, without the need of removing the cover. In such embodiments, condensation on the cover may disturb or prevent visual inspection of the cultivation process. A cover that is particularly preferred in accordance with the present invention is a lid. The lid can be made of glass, metal, plastic or a combination thereof.

Preferably, the gaseous atmosphere is air. In other words, it is preferred according to the present invention if the gaseous composition of the air surrounding the culture vessel is not particularly altered so that the gaseous atmosphere substantially corresponds to the atmosphere of Earth, the composition of which is known to the skilled person. Briefly, dry air contains roughly 78 vol.-% nitrogen, 21 vol.-% oxygen and about 1 vol.-% of other gases, in particular argon and carbon dioxide. In alternative embodiments, the composition of the gaseous atmosphere may differ from the composition of air.

According to the present invention, the BC non-woven is preferably produced in a step-wise or continuous semi-static process. A "step-wise or continuous semi-static" process as used herein, preferably refers to a method in which the BC is produced from a bacterial culture in a culture medium, which is not actively stirred, shacked, or otherwise moved during BC synthesis, in which, however, the BC is continuously produced by the bacterial culture. The fact that the culture medium is not actively stirred, shacked, or otherwise moved during BC synthesis does neither exclude harvesting or removal of BC from the bacterial culture and/or culture vessel during BC synthesis nor adding culture medium and/or constituents of the culture medium during BC biosynthesis. Particularly, in a "step-wise or continuous semi-static" process as used herein, the BC is harvested or removed from the bacterial culture and/or culture vessel more than once during BC synthesis, preferably regularly, step-wise and/or continuously. Particularly, in a "step-wise or continuous semi-static" process as used herein, preferably the culture medium and/or constituents of the culture medium are added more than once, preferably regularly, step-wise and/or continuously during the BC synthesis. In connection therewith a "step-wise or continuous semi-static" process as used herein, preferably is not a batch production method.

Preferably, in an embodiment of the present invention, on average at least 0.125 $m^2$ of BC non-woven, more preferably at least 0.25 $m^2$ of BC non-woven, more preferably at least 0.5 $m^2$ of BC non-woven, more preferably 1 $m^2$ of BC non-woven is harvested or removed from the bacterial culture and/or culture vessel per day and per 1 $m^2$ basal area of culture vessel, preferably regularly, step-wise and/or continuously (harvesting phase), after an initial phase of mechanically-stable BC non-woven fleece generation (incubation phase). Optionally, the basal area corresponds to the area of the air/culture medium interface before cultivation, which may be equivalent to the synthesis area of the culture vessel. That on average an amount of X $m^2$ of BC non-woven is harvested per day and per 1 $m^2$ basal area of culture vessel does not necessarily mean that harvesting is done every day. For example, harvesting might be done every second day and the average amount of BC non-woven that is harvested per day may be determined by dividing the amount of BC non-woven that was harvested (in $m^2$ per $m^2$ basal area of culture vessel) by the number of days of cultivation (2 days in this example).

According to step a) of the method of the present invention, BC is synthesized by incubating a bacterial culture in a culture vessel, wherein the bacterial culture comprises liquid culture medium and BC-synthesizing bacteria.

In general, any BC-synthesizing bacterial strain may be applied in the present invention. However, preferably the BC-synthesizing bacteria are of the strain *Komagatagaibacter xylinum*, also known as *Gluconacetobacter xylinum*. Preferably, the *K. xylinum* strain is selected from the group consisting of the strains ATCC 11142 and DSM 14666. In preferred embodiments, the bacterial culture may comprise a mixture of two bacterial strains or even three bacterial strains. In a preferred embodiment, the bacterial culture comprises a mixture of the *K. xylinum* strains ATCC 11142 and DSM 14666.

Preferably, the culture medium comprises a carbon source, a nitrogen source and a vitamin source and optionally a buffer system. Preferably, the culture medium is an aqueous solution. Preferably, the culture medium substantially consists of a carbon source, a nitrogen source and a vitamin source, an optional buffer system and water, and optionally one or more salts. An optimized composition of the culture medium is set out below. It provides for excellent cultivation results in terms of quality and yield of BC non-woven.

The term "carbon source" refers to carbon containing components that can be utilized, in particular metabolized, by the bacteria. The term "nitrogen source" refers to nitrogen containing components that can be utilized, in particular metabolized, by the bacteria. The term "vitamin source" refers to vitamin containing components that can be utilized by the bacteria. The term "buffer system" refers to components that are useful for minimizing changes of the pH of the culture medium. Preferably, the carbon source is selected from one or more sugars and their derivatives. Preferably, the nitrogen source is peptone. Preferably, the vitamin source is yeast extract. Preferably, the buffer system is disodium hydrogen phosphate and citric acid.

Preferably, the culture medium comprises the carbon source in an amount of at least 10 g/l, more preferably at least 15 g/l based on the volume of the culture medium. Preferably, the culture medium comprises the carbon source in an amount of at most 50 g/l, more preferably at most 30 g/l based on the volume of the culture medium. Particularly preferably, the culture medium comprises the carbon source in an amount of about 20 g/l.

Preferably, the culture medium comprises the nitrogen source in an amount of at least 2 g/l, more preferably at least 4 g/l based on the volume of the culture medium. Preferably, the culture medium comprises the nitrogen source in an amount of at most 10 g/l, more preferably at most 7 g/l based on the volume of the culture medium. Particularly preferably, the culture medium comprises the nitrogen source in an amount of about 5 g/l.

Preferably, the culture medium comprises the vitamin source in an amount of at least 2 g/l, more preferably at least 4 g/l based on the volume of the culture medium. Preferably, the culture medium comprises the vitamin source in an amount of at most 10 g/l, more preferably at most 7 g/l based on the volume of the culture medium. Particularly preferably, the culture medium comprises the vitamin source in an amount of about 5 g/l.

Preferably, the culture medium comprises the buffer system in an amount of least 2 g/l, more preferably at least 3 g/l based on the volume of the culture medium. Preferably, the culture medium comprises the buffer system in an amount of at most 10 g/l, more preferably at most 5 g/l based on the volume of the culture medium. Particularly preferably, the culture medium comprises the buffer system in an amount of about 3.8 g/l.

Particularly preferably, the culture medium comprises 20 g/l glucose, 5 g/l peptone, 5 g/l yeast extract, 2.7 g/l disodium hydrogen phosphate and 1.15 g/l citric acid.

Optionally, the culture medium may be supplemented by additives such as organic components, e.g. starch, chitosan, chitin, collagen, methylcellulose, carboxymethylcellulose, hyaluronic acid and/or alginates, hydroxyethyl cellulose, polyvinylalcohol and/or polyethylenoxide, or inorganic components, e.g. metal oxides, hydroxyapatide and/or graphene. In particular, such additives may be used in accordance with the present invention in order to alter the network structure and/or material properties and/or to produce BC composites. The term "BC non-woven" as used in the present specification comprises such BC non-woven with altered network structure and/or material properties as well as such BC composites.

Preferably, the culture volume is at least 5 l, more preferably at least 50 l, still more preferably at least 200 l, still more preferably at least 400 l, and still more preferably at least 1,000 l. Preferably, the culture volume is at most 20,000 l, more preferably at most 18,000 l, more preferably at most 10,000l, and still more preferably at most 5,000 l. Particularly, the step-wise or continuous semi-static process as described herein may allow for advantageously high culture volumes.

The present inventors found that also the volume of culture medium per basal area of the culture vessel is a factor that has an influence on the efficiency of the process of the invention. If the respective ratio is very high, it is more difficult to keep the culturing conditions constant so that there is a risk that the obtained material is less homogeneous. On the other hand, if there is very little culture medium per basal area of culture vessel, BC may not be obtained with the desired thickness. Preferably, the ratio of the volume of culture medium per basal area of culture vessel is from 1 to 30 l/m$^2$, more preferably 2 to 20 l/m$^2$, more preferably 3 to 10 l/m$^2$.

In preferred embodiments, the method of the present invention enables reduction of the consumption of culture medium. With the method of the present invention, particularly in embodiments in which the culture vessel is covered with a cover, evaporation of culture medium may be strongly reduced or even avoided. Therefore, the amount of culture medium that has to be replaced may be substantially limited to the amount of culture medium that is removed from the culture vessel by the removal of BC. As described in more detail below, the BC non-woven of the present invention comprises large amounts of liquid in its native state. Thus, when BC non-woven is removed from the culture vessel, also culture medium contained within the BC non-woven is removed from the culture vessel. This culture medium is preferably replaced by adding fresh or recycled culture medium to the culture vessel. However, the method of the present invention enables reducing other losses of culture medium as for example by evaporation so that the overall loss of culture medium is strongly reduced.

Furthermore, it should be noted that reduction of evaporation is also advantageous for another reason. Namely, evaporation is normally connected with a change of concentrations of different components of the culture medium. In particular, the concentrations of carbon source, nitrogen source, vitamin source and the optional buffer system generally increase in case of evaporation because it is mainly water that evaporates. In cases of substantial evaporation, the concentration of the culture medium that may optionally be added to the culture vessel according to steps b) and e) of the method of the present invention should be adapted in order to compensate for concentration changes caused by evaporation. This may require complicated measurements and calculations. However, the method of the present invention that preferably drastically reduces evaporation, enables addition of culture medium in steps b) and e) without the need for any adaptions of the concentrations of components.

Preferably, evaporation of culture medium from the culture vessel is at most 2.0 L per m$^2$ culture vessel per day, more preferably at most 1.0 L per m$^2$ culture vessel per day, more preferably at most 0.5 L per m$^2$ culture vessel per day, more preferably at most 0.2 L per m$^2$ culture vessel per day, more preferably at most 0.1 L per m$^2$ culture vessel per day, more preferably at most 0.05 L per m$^2$ culture vessel per day, more preferably at most 0.02 L per m$^2$ culture vessel per day, more preferably at most 0.01 L per m$^2$ culture vessel per day. Preferably, evaporation is measured under laminar air flow conditions and at a temperature of 28° C., or at the conditions applied in the present method.

The culture volumes may also depend on the desired BC synthesis area, and vice versa. The properties of the obtained BC content of the article, such as a non-woven, may also be influenced by the culture vessel and/or synthesis area. Preferably, the culture vessel has a synthesis area of at least 1 cm$^2$, more preferably at least 10 cm$^2$, more preferably at least 100 cm$^2$, more preferably at least 1,000 cm$^2$, more preferably at least 1 m$^2$ and still more preferably at least 10 m$^2$. Preferably, the culture vessel has a synthesis area of at most 50,000 m$^2$, more preferably at most 20,000 m$^2$, more preferably at most 1,000 m$^2$, still more preferably at most 100 m$^2$, still more preferably at most 50 m$^2$. Particularly, the semi-static continuous process as described herein may allow for an advantageously high synthesis area.

Preferably, the culture vessel has a substantially rectangular shape. Preferably, the aspect ratio of length to width of the culture vessel is at least 1.5. More preferably, the aspect ratio of length to width of the culture vessel is at least 2, more preferably at least 3, more preferably at least 5, more preferably at least 10, more preferably at least 15, more preferably at least 20, more preferably at least 25, more preferably at least 30, more preferably at least 50, more preferably at least 100. However, the respective aspect ratio should not be very high. Preferably, that the aspect ratio of length to width of the culture vessel is at most 10,000, more preferably at most 8,000, more preferably at most 5,000, more preferably at most 2,000, more preferably at most 1,000, more preferably at most 500. The inventors found that such aspect ratios are particularly advantageous for the efficiency of the method of the present invention.

Preferably, the culture vessel has a length of at least 100 cm, more preferably at least 200 cm, more preferably at least 500 cm, more preferably at least 1,000 cm. Preferably, the culture vessel has a length of at most 1,000 m, more preferably at most 200 m, more preferably at most 100 m, more preferably at most 50 m, more preferably at most 20 m.

Preferably, the culture vessel has a width of at least 10 cm, more preferably at least 20 cm, more preferably at least 50 cm, more preferably at least 100 cm. Preferably, the culture vessel has a width of at most 100 m, more preferably at most 20 m, more preferably at most 10 m, more preferably at most 5 m, more preferably at most 2 m.

Preferably, the temperature of the culture medium in step a) of the method of the present invention is at least 20° C., more preferably at least 25° C., more preferably at least 28° C. If the incubation temperature is too low, the bacterial strains do not grow properly. Preferably, the temperature of the culture medium in step a) of the method of the present invention is at most 40° C., more preferably at most 35° C., more preferably at most 30° C. If the incubation temperature is too high, the bacterial strains do not grow properly. Preferably, the temperature of the culture medium is controlled by suitable measures as for example a heating device.

Preferably, the temperature of the culture medium is very homogeneous throughout the culture vessel. This is advantageous for obtaining BC non-woven with high efficiency. Furthermore, homogeneity of the obtained BC non-woven is increased. Preferably, the temperature difference between the highest and the lowest temperature of the culture medium in the culture vessel is at most 3 K, more preferably at most 2 K, more preferably at most 1.5, more preferably at most 1 K, more preferably at most 0.5 K, more preferably at most 0.2 K, more preferably at most 0.1 K. If the temperature difference is too high, the homogeneity of the obtained BC non-woven is impaired.

Preferably the incubation time in step a) of the method of the present invention is at least 1 day, more preferably at least 2 days, more preferably at least 3 days. If the incubation time is too short, not enough mechanically stable cellulose is produced. Preferably, the incubation time is at most 10 days, more preferably at most 9 days, more preferably at most 8 days, more preferably at most 7 days, more preferably at most 6 days. Particularly preferably, the incubation time in step a) of the method of the present invention is of from 3 to 6 days. The incubation time may refer to the time that the BC is allowed to grow before removal from the culture vessel starts.

Optionally, according to step b) of the method of the present invention fresh or recycled culture medium may be added and/or consumed culture medium may be removed during the incubation. Recycled culture medium may be obtained from consumed culture medium by adding to the consumed culture medium constituents whose contents are reduced in the consumed culture medium as compared to the original culture medium.

Preferably, fresh or recycled culture medium is added above or below the fluid level of the culture medium in the culture vessel. Particularly preferably, fresh or recycled culture medium is added below the fluid level of the culture medium in the culture vessel. This is advantageous for minimizing disturbance of the bacterial culture and for minimizing structural changes of the BC non-woven that might otherwise occur. Preferably, addition of fresh or recycled culture medium is done below the fluid level with substantially maximum vertical distance from the surface of the culture medium.

Constituents of the culture medium get consumed during incubation of the bacterial culture according to step a) of the method of the present invention. In other words, consumed culture medium is formed during the incubation. Therefore, it is advantageous if fresh culture medium or at least constituents thereof are added during the incubation of the bacterial culture in order to keep the content of the relevant constituents of the culture medium at a substantially constant level. In particular, it is advantageous if the levels of carbon source, nitrogen source, vitamin source and/or the components of the optional buffer system are kept substantially constant. The term "substantially constant" indicates that the concentrations are preferably kept in a range that is sufficient for proper cultivation of the BC-synthesizing bacteria. Preferably, the term "substantially constant" indicates that the concentrations are preferably kept in a range of from 20% to 150%, more preferably of from 30% to 100%, more preferably of from 35% to 80%, more preferably of from 40% to 60% of the initial concentrations at the onset of incubation in step a) of the method of the present invention.

It is preferable that the fresh culture medium that is optionally added according to step b) of the method of the present invention has a similar composition as the culture medium at the onset of incubation in step a) of the method of the present invention as described above. More preferably, the fresh culture medium has substantially the same composition as the culture medium at the onset of incubation in step a) of the method of the present invention.

Preferably, the fresh or recycled culture medium that is added according to step b) has a temperature that differs from the temperature of the pre-existing culture medium in the culture vessel by at most ±25 K, more preferably at most ±10 K, more preferably at most ±8 K, more preferably at most ±5 K, more preferably by at most ±2 K, more preferably by at most ±1 K. Adding fresh or recycled culture medium with a substantially different temperature than the pre-existing culture medium would impair homogeneity and quality of the BC non-woven.

Furthermore, during incubation of the bacterial culture the BC-synthesizing bacteria may produce metabolites that are potentially disturbing the cultivation conditions. Therefore, it is advantageous if consumed culture medium is removed during incubation.

Particularly preferably, fresh culture medium is added and consumed culture medium is removed during the incubation. Thereby, the above-described advantages of adding fresh culture medium and removing consumed culture medium can be achieved and furthermore the culture volume can be kept at a substantially constant level.

According to step c) of the method of the present invention, produced BC non-woven having an average thickness of at least 0.5 mm is removed from the culture vessel. An average thickness of at least 0.5 mm indicates that production of BC non-woven is finished. The thickness of the removed BC non-woven should not be too high. In particular, a low thickness is advantageous for a variety of uses of the BC. Preferably, the average thickness of the removed BC is at most 30 mm, more preferably at most 20 mm, more preferably at most 10 mm, more preferably at most 5 mm, more preferably at most 4 mm, more preferably at most 3 mm. The present inventors found that the method of the present invention surprisingly enables obtaining mechanically stable BC non-woven with particularly low thickness. Particularly preferably, the average thickness of the removed non-woven is from 0.5 to 4 mm.

The inventors found that by the method of the present invention BC non-woven can be obtained with increased space-time-yield. In other words, BC non-woven with good tensile strength can be obtained after comparably short production times as compared to the prior art. Furthermore, the BC non-woven of the present invention has an improved specific tensile strength determined as the ratio of tensile strength and average thickness of the BC non-woven. In other words, the BC non-woven of the present invention has a high tensile strength even if the thickness of the BC non-woven is comparably low. This is advantageous for many applications, in particular if the BC non-woven is to be applied to the skin for example as a wound dressing or cosmetic pad, particularly as eye pad, forehead mask, eye mask, face mask, or the like. Such articles should be comparably thin in order to enable fixation of the articles to the skin only by means of adhesive forces between article and skin. Thick articles may require additional fixation means because they are heavier so that the adhesive forces between article and skin may be too small for compensating gravitational forces.

Synthesis of BC in the culture vessel continues during removal of the produced BC non-woven and non-finished BC non-woven remains in the culture vessel and is separated from the BC non-woven that is removed. The term "non-finished BC non-woven" indicates that the desired average thickness has not yet been reached.

Preferably, the produced BC non-woven is removed from the culture vessel in step c) by pulling and/or pushing the BC non-woven out of the culture vessel in a direction substantially parallel to the interface of BC and gaseous atmosphere. This way of removal is advantageous for minimizing disturbance of the bacterial culture and for minimizing structural changes of the BC non-woven that might otherwise occur. In particular, structural changes of the BC network may be minimized or even avoided by this way of removal.

Preferably, removal of produced BC non-woven in step c) takes place after at least 1 day, more preferably at least 2 days, more preferably at least 3 days of incubation (incubation time). If the incubation time is too short, not enough mechanically stable cellulose is produced. Preferably, removal of produced BC non-woven in step c) takes place after at most 10 days, more preferably at most 9 days, more preferably at most 8 days, more preferably at most 7 days, more preferably at most 6 days of incubation. Preferably, removal of BC non-woven in step c) takes place after 3 to 6 days of incubation.

Preferably, separation of non-finished BC non-woven remaining in the culture vessel and produced BC non-woven that is removed from the culture vessel is achieved by cutting. Preferably, separation of non-finished BC non-woven remaining in the culture vessel and produced BC non-woven that is removed from the culture vessel is achieved by fluid jet cutting, in particular by water jet cutting. Fluid jet cutting is advantageous for obtaining cut edges with particularly smooth surface. The fluid jet is preferably provided with a pressure of at least 1,000 and at most 4,000 bar. The fluid jet preferably has a diameter of from 100 μm to 300 μm, more preferably of from 125 μm to 200 μm, most preferably of about 150 μm. The present inventors found that also an advantageous cutting speed may further improve the results. Preferably, the cutting speed is at least 0.05 cm/sec, more preferably at least 0.1 cm/sec, more preferably at least 0.2 cm/sec, more preferably at least 0.5 cm/sec, more preferably at least 1.0 cm/sec. Preferably, the cutting speed is at most 30 cm/sec, more preferably at most 20 cm/sec, more preferably at most 10 cm/sec. Particularly preferably, the cutting speed is from 0.05 cm/sec to 30 cm/sec, more preferably from 1 cm/sec to 10 cm/sec. Such cutting with a fluid jet is advantageous compared to cutting methods usually provided in the art, for example, thermal cutting with a laser or the like, or mechanical cutting. Such methods of the prior art usually compromise the structure of the BNC material. The cutting according to the present invention, however, provides a high quality of the cutting edge without destruction of the surrounding BNC. FIG. 1 shows scanning electron microscope images that allow comparison of cut edges obtained by fluid jet cutting with cut edges obtained by cutting with a scalpel. It can be seen that the surface of the cut edge obtained by fluid jet cutting is particularly smooth, in particular smoother than the surface of the cut edge obtained by cutting with a scalpel.

The present invention also relates to the use of fluid jet cutting for cutting BC.

In addition to steps a) to c), the method of the present invention preferably comprises further steps, in particular steps d) to g) as described above.

According to step d) of the method of the present invention, synthesis of BC is continued in the culture vessel by continuation of incubation of the bacterial culture in the culture vessel.

Preferably, the temperature of the culture medium in step d) of the method of the present invention is at least 20° C., more preferably at least 25° C., more preferably at least 28° C. If the incubation temperature is too low, the bacterial strains do not grow properly. Preferably, the temperature of the culture medium in step d) of the method of the present invention is at most 40° C., more preferably at most 35° C., more preferably at most 30° C. If the incubation temperature is too high, the bacterial strains do not grow properly. Preferably, the temperature of the culture medium is controlled by suitable measures as for example a heating device. Particularly preferably, the temperature of the culture medium is controlled by a temperature control system comprising a heating device and at least one temperature sensor.

Preferably the incubation time in step d) of the method of the present invention is at least 12 hours, more preferably at least 24 hours, more preferably at least 36 hours, more preferably at least 48 hours prior the start of step f). If the incubation time is too short, not enough cellulose is produced. Preferably, the incubation time in step d) is at most 100 hours, more preferably at most 90 hours, more preferably at most 80 hours, more preferably at most 70 hours, more preferably at most 60 hours prior the start of step f). If the incubation time is very long, the thickness of the produced BC non-woven will be very large which is disadvantageous for several applications, in particular if the BC non-woven is to be applied to the skin for example as a wound dressing or cosmetic pad. Furthermore, a long incubation time renders the method inefficient.

Optionally, according to step e) of the method of the present invention fresh or recycled culture medium may be added and/or consumed culture medium may be removed during the continued incubation. Recycled culture medium may be obtained from consumed culture medium by adding to the consumed culture medium constituents whose contents are reduced in the consumed culture medium as compared to the original culture medium.

Preferably, fresh or recycled culture medium is added above or below the fluid level of the culture medium in the culture vessel. Particularly preferably, fresh or recycled culture medium is added below the fluid level of the culture medium in the culture vessel. This is advantageous for minimizing disturbance of the bacterial culture and for minimizing structural changes of the BC non-woven that might otherwise occur.

Constituents of the culture medium get consumed during incubation of the bacterial culture according to step d) of the method of the present invention. Therefore, it is advantageous if fresh culture medium or at least constituents thereof are added during the incubation of the bacterial culture in order to keep the content of the relevant constituents of the culture medium at a substantially constant level. In particular, it is advantageous if the levels of carbon source, nitrogen source, vitamin source and/or the components of the optional buffer system are kept substantially constant. The term "substantially constant" indicates that the concentrations are preferably kept in a range that is sufficient for proper continued cultivation of the BC-synthesizing bacteria. Preferably, the term "substantially constant" indicates that the concentrations are preferably kept in a range of from 20% to 150%, more preferably of from 30% to 100%, more preferably of from 35% to 80%, more preferably of from 40% to 60% of the initial concentrations at the onset of incubation in step a) of the method of the present invention.

It is preferable that the fresh culture medium that is optionally added according to step e) of the method of the present invention has a similar composition as the culture medium at the onset of incubation in step d) of the method of the present invention as described above. More preferably, the fresh culture medium has substantially the same composition as the culture medium at the onset of incubation in step d) of the method of the present invention.

Preferably, the fresh or recycled culture medium that is added according to step e) has a temperature that differs from the temperature of the pre-existing culture medium in the culture vessel by a most ±25 K, more preferably at most ±10 K, more preferably at most ±8 K, more preferably at most ±5 K, more preferably by at most ±2 K, more preferably by at most ±1 K. Adding fresh or recycled culture medium with a substantially different temperature than the pre-existing culture medium would impair homogeneity and quality of the BC non-woven.

Furthermore, during incubation of the bacterial culture the BC-synthesizing bacteria may produce metabolites that are potentially disturbing the cultivation conditions. Therefore, it is advantageous if consumed culture medium is removed during continued incubation.

Particularly preferably, fresh culture medium is added and consumed culture medium is removed during the incubation. Thereby, the above-described advantages of adding fresh culture medium and removing consumed culture medium can be achieved and furthermore the culture volume can be kept at a substantially constant level.

According to step f) of the method of the present invention, produced BC non-woven having an average thickness of at least 0.5 mm is removed from the culture vessel. An average thickness of at least 0.5 mm indicates that production of BC non-woven is finished. The thickness of the removed BC non-woven should not be too high. In particular, a low thickness is advantageous for a variety of uses of the BC. Preferably, the average thickness of the removed BC is at most 30 mm, more preferably at most 20 mm, more preferably at most 10 mm, more preferably at most 5 mm, more preferably at most 4 mm. The present inventors found that the method of the present invention surprisingly enables obtaining mechanically stable BC non-woven with particularly low thickness. Particularly preferably, the average thickness of the removed non-woven is from 0.5 to 4 mm.

The inventors found that by the method of the present invention BC non-woven can be obtained with increased space-time-yield. In other words, BC non-woven with good tensile strength can be obtained after comparably short production times as compared to the prior art. Furthermore, the BC non-woven of the present invention has an improved specific tensile strength determined as the ratio of tensile strength and average thickness of the BC non-woven.

Preferably, synthesis of BC in the culture vessel continues during removal of the produced BC non-woven and preferably non-finished BC non-woven remains in the culture vessel and is separated from the BC non-woven that is removed.

Preferably, the produced BC non-woven is removed from the culture vessel in step f) by pulling and/or pushing the BC non-woven out of the culture vessel in a direction substantially parallel to the interface of BC and gaseous atmosphere. This way of removal is advantageous for minimizing disturbance of the bacterial culture and for minimizing structural changes of the BC non-woven that might otherwise occur. In particular, structural changes of the BC network may be minimized or even avoided by this way of removal.

Preferably, removal of produced BC non-woven in step f) takes place after at least 12 hours, more preferably at least 24 hours, more preferably at least 36 hours, more preferably at least 48 hours of continued incubation according to step d) of the method of the present invention. If the incubation time is too short, not enough cellulose is produced. Preferably, removal of produced BC non-woven in step f) takes place after at most 100 hours, more preferably at most 90 hours, more preferably at most 80 hours, more preferably at most 70 hours, more preferably at most 60 hours of continued incubation.

Preferably, separation of non-finished BC non-woven remaining in the culture vessel and produced BC non-woven that is removed from the culture vessel is achieved by cutting. Preferably, separation of non-finished BC non-woven remaining in the culture vessel and produced BC non-woven that is removed from the culture vessel is achieved by fluid jet cutting. Fluid jet cutting is advantageous for obtaining cut edges with particularly smooth surface. FIG. 1 shows scanning electron microscope images that allow comparison of cut edges obtained by fluid jet cutting with cut edges obtained by cutting with a scalpel. It can be seen that the surface of the cut edge obtained by fluid jet cutting is particularly smooth, in particular smoother than the surface of the cut edge obtained by cutting with a scalpel.

Preferably, steps d) to f) of the method of the present invention are repeated at least once. More preferably, steps d) to f) are repeated at least twice, more preferably at least three times, more preferably at least four times, more preferably at least five times, more preferably at least ten times, more preferably at least twenty-five times. However, steps d) to f) should not be repeated extremely often. Preferably, steps d) to f) are repeated at most hundred times, more preferably at most fifty times. If steps d) to f) are repeated extremely often, the concentration of metabolites of bacteria may be increased to such an extent (in particular due to lack of removal or due to incomplete removal) that the processes taking place in the culture vessel (in particular synthesis of BC) may be impaired.

Preferably, the time span from the beginning of synthesis of BC non-woven according to step a) until the completion of the last repetition according to step g) is from 1 to 12 months, more preferably from 2 to 6 months, more preferably from 3 to 5 months.

According to the method of the present invention, preferably at least during steps a) and d), more preferably at least during steps a), b), d) and e), more preferably during steps a) to g) the gaseous atmosphere above the bacterial culture is kept at a temperature that is at most 10 K below the highest temperature of the culture medium in the culture vessel within a distance from the interface of BC and gaseous atmosphere of from 0 to 2 cm measured perpendicular to the interface. The present inventors found that controlling the temperature of the gaseous atmosphere in the indicated range contributes to increasing the efficiency of BC non-woven production. In particular, the incubation time necessary for obtaining BC non-woven having an average thickness of at least 0.5 mm can be substantially reduced.

Control of the temperature of the gaseous atmosphere can be achieved by a variety of different measures according to the present invention. In preferred embodiments, the culture vessel is covered with a cover. Alternatively or additionally, the gaseous atmosphere above the culture vessel is selectively heated. It is also possible to keep the gaseous atmosphere of the entire room in which the culture vessel is located at the desired temperature. Moreover, temperature control may be applied to several culture vessels, in particular at least two, more preferably at least three culture vessels, simultaneously. For example, several culture vessels may be placed in a single room and the gaseous atmosphere of the entire room may be controlled. It is also possible to control the gaseous atmosphere of more than one culture vessel without controlling the atmosphere of the entire room, for example by covering several culture vessels with a common cover or with separate covers. Furthermore, different measures can be combined in accordance with the present invention. For example, in particularly preferred embodiments the gaseous atmosphere above the culture vessel is heated and additionally the culture vessel is covered with a cover.

Preferably, at least during steps a) and d), more preferably at least during steps a), b), d) and e), more preferably during steps a) to g) the gaseous atmosphere above the bacterial culture is kept at a temperature that is at most 8 K, more preferably at most 5 K, more preferably at most 4 K, more preferably at most 3 K, more preferably at most 2 K, more preferably at most 1 K, more preferably at most 0.5 K, more preferably at most 0.1 K below the highest temperature of the culture medium in the culture vessel within a distance from the interface of BC and gaseous atmosphere of from 0 to 2 cm measured perpendicular to the interface. Controlling the temperature in the indicated ranges is advantageous for the efficiency of BC non-woven production. In particularly preferred embodiments, the gaseous atmosphere above the bacterial culture is kept at a temperature that is at least as high as the temperature of the culture medium in the culture vessel within a distance from the interface of BC and gaseous atmosphere of from 0 to 2 cm measured perpendicular to the interface. Preferably, the gaseous atmosphere above the bacterial culture is kept at a temperature that is at most 10 K, more preferably at most 5 K, more preferably at most 4 K, more preferably at most 3 K, more preferably at most 2 K, more preferably at most 1 K, more preferably at most 0.5 K, more preferably at most 0.1 K above the highest temperature of the culture medium in the culture vessel within a distance from the interface of BC and gaseous atmosphere of from 0 to 2 cm measured perpendicular to the interface. Preferably, the gaseous atmosphere above the bacterial culture is kept at a temperature of at most ±10 K, more preferably at most ±5 K, more preferably at most ±4 K, more preferably at most ±3 K, more preferably at most ±2 K, more preferably at most ±1 K, more preferably at most ±0.5 K, more preferably at most ±0.1 K as compared to the temperature of the culture medium in the culture vessel within a distance from the interface of BC and gaseous atmosphere of from 0 to 2 cm measured perpendicular to the interface.

Preferably, at least during steps a) and d), more preferably at least during steps a), b), d) and e), more preferably during steps a) to g) the gaseous atmosphere above the bacterial culture is kept at a temperature that is at most 10 K, more preferably at most 8 K, more preferably at most 5 K, more preferably at most 4 K, more preferably at most 3 K, more preferably at most 2 K, more preferably at most 1 K, more preferably at most 0.5 K, more preferably at most 0.1 K below the highest temperature of the culture medium in the culture vessel within a distance from the interface of BC and gaseous atmosphere of from 0 to 5 cm measured perpendicular to the interface. Controlling the temperature in the indicated ranges is advantageous for the efficiency of BC non-woven production. In particularly preferred embodiments, the gaseous atmosphere above the bacterial culture is kept at a temperature that is at least as high as the temperature of the culture medium in the culture vessel within a distance from the interface of BC and gaseous atmosphere of from 0 to 5 cm measured perpendicular to the interface. Preferably, the gaseous atmosphere above the bacterial culture is kept at a temperature that is at most 10 K, more preferably at most 5 K, more preferably at most 4 K, more preferably at most 3 K, more preferably at most 2 K, more preferably at most 1 K, more preferably at most 0.5 K, more preferably at most 0.1 K above the highest temperature of the culture medium in the culture vessel within a distance from the interface of BC and gaseous atmosphere of from 0 to 5 cm measured perpendicular to the interface. Preferably, the gaseous atmosphere above the bacterial culture is kept at a temperature of at most ±10 K, more preferably at most ±5 K, more preferably at most ±4 K, more preferably at most ±3 K, more preferably at most ±2 K, more preferably at most ±1 K, more preferably at most ±0.5 K, more preferably at most ±0.1 K as compared to the temperature of the culture medium in the culture vessel within a distance from the interface of BC and gaseous atmosphere of from 0 to 5 cm measured perpendicular to the interface.

Preferably, at least during steps a) and d), more preferably at least during steps a), b), d) and e), more preferably during steps a) to g) the gaseous atmosphere above the bacterial culture is kept at a temperature that is at most 10 K, more preferably at most 8 K, more preferably at most 5 K, more preferably at most 4 K, more preferably at most 3 K, more preferably at most 2 K, more preferably at most 1 K, more preferably at most 0.5 K, more preferably at most 0.1 K below the highest temperature of the culture medium in the culture vessel within a distance from the interface of BC and gaseous atmosphere of from 0 to 10 cm measured perpendicular to the interface. Controlling the temperature in the indicated ranges is advantageous for the efficiency of BC non-woven production. In particularly preferred embodiments, the gaseous atmosphere above the bacterial culture is kept at a temperature that is at least as high as the temperature of the culture medium in the culture vessel within a distance from the interface of BC and gaseous atmosphere of from 0 to 10 cm measured perpendicular to the interface. Preferably, the gaseous atmosphere above the bacterial culture is kept at a temperature that is at most 10 K, more preferably at most 5 K, more preferably at most 4 K, more preferably at most 3 K, more preferably at most 2 K, more preferably at most 1 K, more preferably at most 0.5 K, more preferably at most 0.1 K above the highest temperature of the culture medium in the culture vessel within a distance from the interface of BC and gaseous atmosphere of from 0 to 10 cm measured perpendicular to the interface. Preferably, the gaseous atmosphere above the bacterial culture is kept at a temperature of at most ±10 K, more preferably at most ±5 K, more preferably at most ±4 K, more preferably at most ±3 K, more preferably at most ±2 K, more preferably at most ±1 K, more preferably at most ±0.5 K, more preferably at most ±0.1 K as compared to the temperature of the culture medium in the culture vessel within a distance from the interface of BC and gaseous atmosphere of from 0 to 10 cm measured perpendicular to the interface.

A temperature of the gaseous atmosphere that is slightly higher than the temperature of the culture medium is particularly preferred in embodiments in which the culture vessel is covered with a transparent cover for enabling visual inspection of the production process because such temperature regimen prevents or at least substantially reduces condensation of liquid on the surfaces of the cover that face the interior of the culture vessel. In embodiments, in which the cover is not transparent, it is also advantageous if the temperature of the gaseous atmosphere is slightly higher than the temperature of the culture medium because condensation does not only compromise visual inspection but may also lead to formation of drops of condensate that may fall into the culture vessel and thereby disturb BC non-woven production. Furthermore, a temperature of the gaseous atmosphere that is slightly higher than the temperature of the culture medium is also advantageous in embodiments, in which the culture vessel is not covered with a cover, because this may support keeping the temperature of the culture medium substantially constant.

Preferably, at least during steps a) and during optional step d), more preferably at least during steps a), b) and during optional steps d) and e), more preferably during steps a) to c) and during optional steps d) to g) the gaseous atmosphere above the bacterial culture is kept at a relative humidity of at least 70% within a distance from the interface of BC and gaseous atmosphere of from 0 to 2 cm measured perpendicular to the interface. This means that the humidity condition is met throughout the mentioned distance from the interface, i.e. at all distances within the range of from 0 to 2 cm. Generally, the humidity decreases with increasing distance from the interface. The present inventors found that keeping the gaseous atmosphere above the bacterial culture at a relative humidity of at least 70% within a distance from the interface of BC and gaseous atmosphere of from 0 to 2 cm measured perpendicular to the interface may help improving the surface quality and homogeneity of properties of the produced BC non-woven. In particular, a high relative humidity may help preventing or at least substantially reducing dehydration and withering at the surface of the BC non-woven. Withering is disadvantageous because it may be associated with shriveling, a reduced porosity and impaired mechanical properties of the BC non-woven. In particular, water permeability and/or breathability of the BC non-woven may be impaired by withering. Furthermore, the surface roughness of the BC non-woven may be substantially increased by withering.

Control of the humidity of the gaseous atmosphere can be achieved by a variety of different measures according to the present invention. In preferred embodiments, the culture vessel is covered with a cover. In alternative embodiments, the gaseous atmosphere above the culture vessel is selectively heated and/or humidified. Humidification is preferably done with a humidifier and may involve vaporization and/or spraying means. It is also possible to keep the gaseous atmosphere of the entire room in which the culture vessel is located at the desired high relative humidity. However, this may be disadvantageous in certain embodiments, in particular in embodiments that require production of the BC non-woven under controlled level of contamination as for example in a cleanroom. Therefore, in such embodiments it is preferable that not the gaseous atmosphere of the entire room in which the culture vessel is located is kept at the desired high relative humidity but that rather keeping the gaseous atmosphere above the bacterial culture at a high relative humidity is supported by covering the culture vessel with a cover. It is also possible to control the humidity of the gaseous atmosphere of more than one culture vessel without controlling the atmosphere of the entire room. This may be achieved for example by covering several culture vessels with a common cover or with separate covers. Moreover, different measures can be combined in accordance with the present invention. For example, in particularly preferred embodiments the gaseous atmosphere above the culture vessel is heated and/or humidified and additionally the culture vessel is covered with a cover.

Preferably, at least during steps a) and during optional step d), more preferably at least during steps a), b) and during optional steps d) and e), more preferably during steps a) to c) and during optional steps d) to g) the gaseous atmosphere above the bacterial culture is kept at a relative humidity of at least 80%, more preferably of at least 85%, more preferably of at least 90%, more preferably of at least 92%, more preferably at least 95%, more preferably at least 98%, more preferably at least 99% within a distance from the interface of BC and gaseous atmosphere of from 0 to 2 cm measured perpendicular to the interface. Controlling the relative humidity in the indicated ranges may help improving the surface quality of the produced BC non-woven. In particular, a high relative humidity may help preventing or at least substantially reducing drying out and withering of the surface of the BC non-woven.

Preferably, at least during steps a) and during optional step d), more preferably at least during steps a), b) and during optional steps d) and e), more preferably during steps a) to c) and during optional steps d) to g) the gaseous atmosphere above the bacterial culture is kept at a relative humidity of at least 70%, more preferably of at least 80%, more preferably of at least 85%, more preferably of at least 90%, more preferably at least 92%, more preferably at least 95%, more preferably at least 98%, more preferably at least 99% within a distance from the interface of BC and gaseous atmosphere of from 0 to 5 cm measured perpendicular to the interface. Controlling the relative humidity in the indicated ranges may help improving the surface quality of the produced BC non-woven. In particular, a high relative humidity may help preventing or at least substantially reducing drying out and withering of the surface of the BC non-woven.

Preferably, at least during steps a) and during optional step d), more preferably at least during steps a), b) and during optional steps d) and e), more preferably during steps a) to c) and during optional steps d) to g) the gaseous atmosphere above the bacterial culture is kept at a relative humidity of at least 70%, more preferably of at least 80%, more preferably of at least 85%, more preferably of at least 90%, more preferably at least 92%, more preferably at least 95%, more preferably at least 98%, more preferably at least 99% within a distance from the interface of BC and gaseous atmosphere of from 0 to 10 cm measured perpendicular to the interface. Controlling the relative humidity in the indicated ranges may help improving the surface quality of the produced BC non-woven. In particular, a high relative humidity may help preventing or at least substantially reducing drying out and withering of the surface of the BC non-woven.

Covering the culture vessel with a cover is also advantageous for another reason. Namely, covering the culture vessel with a cover may reduce the volumetric flow rate of gaseous atmosphere entering the volume above the culture vessel in which temperature or temperature and relative humidity are kept at the desired levels. The term "volumetric flow rate" indicates the volume of fluid, in particular of gaseous atmosphere, which passes per unit of time. The present inventors found that air flow above the bacterial culture may result in decreased efficiency of BC non-woven production. Furthermore, the surface quality of the BC non-woven may be reduced by air flow above the bacterial culture. In particular, BC formation may be inhomogeneous so that the BC non-woven comprises distinct spots of BC having denser or less dense network structure. Moreover, the surface of the BC non-woven may be uneven due to the inhomogeneous network formation as well as due to partial drying out of the surface. Therefore, it is preferable that the volumetric flow rate of gaseous atmosphere entering the volume above the culture vessel in which temperature or temperature and relative humidity are kept at the desired levels is restricted. Restriction of such volumetric flow rate may be achieved or at least supported by covering the culture vessel with a cover. Covering the vulture vessel with a cover is particularly advantageous in embodiments that require production of the BC non-woven under controlled level of contamination as for example in a cleanroom, in particular a laminar flow cleanroom. Laminar flow cleanrooms are associated with a particularly large flow of gaseous atmosphere that might be disadvantageous to yield and/or quality of BC non-woven. For example, cleanrooms of classes (ISO) 1 to 5 have air flow velocities of from 0.2 to 0.5 m/s. Cleanrooms of classes 6, 7, 8 and higher classes have air changes per hour of from 160 to 10 $m^3/m^2 \cdot h$. Therefore, it is particularly advantageous in embodiments in which the BC non-woven is produced in a cleanroom if the flow of gaseous atmosphere above the bacterial culture is restricted.

Reduction of flow of gaseous atmosphere above the bacterial culture may be achieved by covering the culture vessel with a cover. Alternatively or additionally, the flow of gaseous atmosphere above the bacterial culture may be reduced by a specific air flow regime that prevents strong air flow above the bacterial culture. Such air flow regime may be achieved by use of elements that redirect air flow so that air flow above the bacterial culture is reduced.

The volume above the culture vessel in which temperature or temperature and relative humidity are kept at the desired levels can roughly be described as being defined by six faces, namely (i) the interface of BC and gaseous atmosphere, (ii) the upper face of the volume being essentially parallel to the interface of BC and gaseous atmosphere, and (iii) to (vi) four side faces being essentially perpendicular to faces (i) and (ii) of the volume.

When it is stated in the present specification that the culture vessel is covered with a cover, this does not mean that necessarily all faces (ii) to (vi) are covered. In particular in embodiments in which the major purpose of covering is reducing air flow into the volume from the top, it may be sufficient if only the upper face (ii) of the volume is covered. Moreover, in embodiments in which the major purpose of covering is reducing air flow into the volume from the side, it may be sufficient if only one or more of side faces (iii) to (vi), in particular all side faces (iii) to (vi) may be covered. However, in other embodiments of the present invention, in particular in embodiments in which relative humidity should be tightly controlled, it may be advantageous that the upper face (ii) and the side faces (iii) to (vi) are covered.

In embodiments in which the culture vessel is covered with a cover, it is preferable that the cover is transparent in order to enable optical evaluation of the process without the need for removal of the cover.

In preferred embodiments, the volumetric flow rate of gaseous atmosphere entering the volume above the culture vessel in which temperature or temperature and relative humidity are kept at the defined levels is, at a pressure of 1013.25 hPa and a temperature of 20° C., less than 1 $dm^3$ per minute and per $m^2$ of the interface at which gaseous atmosphere may enter the volume above the culture vessel in which temperature or temperature and relative humidity are kept at the defined levels.

Preferably, with the method of the present invention a flat BC non-woven is obtained with a yield of 0.1 to 1 m per day of cultivation and per m length of the reactor with a thickness of 15 mm to 0.5 mm.

The method of the present invention may further comprise the step of sterilizing the BC non-woven after removal from the culture vessel in steps c) and/or f) of the method of the present invention. Sterilization of the BC non-woven is advantageous for a variety of applications of the BC non-woven, in particular for dermatological applications, cosmetic applications, diagnostic applications (for example cell culture systems), technical applications (membranes) and for medical applications (for example wound coverings or skin implants). The BC non-woven is preferably sterilized by irradiation with electrons (beta radiation), by irradiation with gamma radiation or by exposure to steam. However, exposure to steam is less preferred because it requires that packages containing BC non-woven are open due to expansion caused by the heat so that there is a substantial risk of re-contamination occurring after sterilization before the packages can be closed and sealed. In contrast, sterilization by irradiation may be done with closed and sealed packages so that re-contamination does not occur. Particularly preferably, the BC non-woven is sterilized by irradiation with electrons, in particular with an electron beam (herein referred to as "e-beam").

The present inventors found that e-beam sterilization is particularly advantageous for sterilizing the BC non-woven because the influence of e-beam sterilization on the network structure of the BC is minimal in comparison to the sterilization with gamma radiation. Therefore, the quality of BC non-woven sterilized with e-beam is improved in comparison to BC non-woven sterilized with gamma radiation. The finding that e-beam sterilization does not compromise the network structure of the BC non-woven was particularly unexpected because it was known that sterilization with gamma radiation has an undesired influence on the BC network structure and on the quality of the BC non-woven so that sterilization with radiation was in general expected to be disadvantages. The fact that e-beam sterilization (beta radiation) is advantageous was therefore particularly surprising. FIG. 2 shows that e-beam sterilization does not compromise the BC network structure in comparison to sterilization by steam exposure.

The present invention also relates to the use of e-beam for sterilization of BC. Preferably, the BC non-woven is sterilized with a dose of from 10 to 50 kGy, more preferably about 15 to 25 kGy. If the dose is too high, the BC network structure might get compromised. If the dose is too low, the BC non-woven may not be sufficiently sterilized.

The present invention also relates to a BC non-woven, in particular a BC non-woven produced by the method of the present invention.

Preferably, the BC non-woven in its native state comprises BC in an amount of at most 15%, preferably of at most 5% by weight. More preferably, the BC non-woven in its native state comprises BC in an amount of from 0.5 to 1.5% by weight. The term "native state" refers to the state of the BC non-woven upon removal from the culture vessel. The BC proportion of the BC non-woven may be increased by at least partial removal of fluid. Notably, BC non-woven in which the BC proportion has been increased by at least partial removal of fluid is not in its native state according to the present invention.

The sum of fluid and BC, in the native state BC non-woven, preferably is at least 80% by weight, in particular at least 90% by weight, in particular at least 95% by weight. In an embodiment the sum of the constituents fluid and BC in the BC non-woven, preferably are essentially 100%. In other words, the BC non-woven may essentially consist of fluid and BC. Optionally, BC non-woven consists of fluid, BC and one or several additives such as organic components, e.g. starch, chitosan, chitin, collagen, methylcellulose, carboxymethylcellulose, hyaluronic acid and/or alginates, hydroxyethyl cellulose, polyvinylalcohol and/or polyethylenoxide, or inorganic components, e.g. metal oxides, hydroxylapatite and/or graphene. Additives may be embedded into the BC network and/or attached to the BC network during production of the BC non-woven.

Upon removal from the culture vessel, the fluid is essentially the culture medium. For various applications, the culture medium is preferably replaced by a different fluid, in particular by water and/or a water-based fluid comprising water, particularly de-ionized water, in an amount of at least 85%, and still more preferably 99%.

A relatively low average thickness of the BC non-woven allows for a couple of applications, particularly applications of BC non-woven in its native state, that means without reduction of the fluid content (for example by mechanical impact), in particular for dermatological applications, cosmetic applications, diagnostic applications (for example cell culture systems), technical applications (membranes), for medical applications (for example wound coverings or skin implants) and pharmaceutical applications (for example drug carrier systems). However, an article having an average thickness, which is too low, may more easily tear. The thickness of the BC non-woven preferably is in average at least 0.5 mm, more preferably at least 0.8 mm, still more preferably at least 1.0 mm, still more preferably at least 1.5 mm, and still more preferably at least 2.0 mm. On the other hand, BC non-woven having an average thickness, which is very high, may disadvantageous for certain applications, in particular dermatological applications. The reason is that a very high thickness may cause an uncomfortable feeling and may not adhere to the skin without the need for further adherence or fixation means. The average thickness of the BC non-woven preferably is at most 8.0 mm, more preferably at most 6.0 mm, still more preferably at most 5.0 mm. The average thickness of the BC non-woven can be determined by usual methods known to the person skilled in the art, comprising e.g. vernier caliper measurements. The BC characteristics allow for thin non-woven at good tensile strength.

Preferably, the BC fibers of the BC non-woven have an average diameter of from 30 to 250 nm. The diameter is preferably determined from scanning electron microscopy (SEM) pictures.

The volumetric mass density of the BC non-woven, particularly of the BC content of the BC non-woven, is at least 0.50 g/cm$^3$, preferably at least 0.55 g/cm$^3$. The volumetric mass density of the BC non-woven, particularly of the BC content of the BC non-woven, is at most 1.50 g/cm$^3$, preferably at most 1.25 g/cm$^3$.

The volumetric mass density of the BC non-woven, particularly of the BC content of the BC non-woven, preferably is from at least 0.50 g/cm$^3$ to at most 1.50 g/cm$^3$, more preferably from at least 0.55 g/cm$^3$ to at most 1.50 g/cm$^3$, still more preferably from at least 0.50 g/cm$^3$ to at most 1.25 g/cm$^3$, and most preferably from at least 0.55 g/cm$^3$ to at most 1.25 g/cm$^3$.

The weight-average molecular weight $M_w$ of the BC non-woven, particularly of the BC of the BC non-woven, preferably is at most 1,500,000 g/mol, more preferably at most 1,200,000 g/mol, more preferably at most 1,000,000 g/mol, more preferably at most 900,000 g/mol, at most 850,000 g/mol, at most 800,000 g/mol, most preferably at most 780,000 g/mol. The weight-average molecular weight $M_w$ of the BC non-woven, particularly of the BC of the BC non-woven, preferably is at least 100,000 g/mol, preferably at least 250,000 g/mol, at least 300,000 g/mol, at least 400,000 g/mol, most preferably at least 500,000 g/mol. If the weight-average molecular weight $M_w$ is very low, the desired polydispersity index may not be achieved as described below.

The number-average molecular weight $M_n$ of the BC non-woven, particularly of the BC of the BC non-woven, preferably is at most 500,000 g/mol, preferably at most 400,000 g/mol, at most 450,000 g/mol, at most 400,000 g/mol, most preferably at most 360,000 g/mol. If the number-average molecular weight $M_n$ is very high, the desired polydispersity index may not be achieved as described below. The number-average molecular weight $M_n$ of the BC non-woven, particularly of the BC of the BC non-woven, preferably is at least 100,000 g/mol, preferably at least 150,000 g/mol, at least 200,000 g/mol, at least 250,000 g/mol, most preferably at least 300,000 g/mol. If the number-average molecular weight $M_n$ is very low, the stability of the material may be impaired.

The degree of polymerization is the average number of monomeric units in the BC polymers of a specific BC network. It can be expressed as the ratio of the number-average molecular weight of the respective BC polymers to the molecular weight of the monomeric unit.

The polydispersity index (PDI) is a measure of the heterogeneity of the molecular mass distribution of the BC polymers of a respective BC network. It is calculated as the ratio of the weight-average molecular weight to the number-average molecular weight of the respective BC polymers. Higher PDI values indicate a broader molecular weight distribution of the BC polymers of a BC network. The length of the cellulose chains of the article are preferably relatively uniform, which may be reflected by a relatively low polydispersity index ($M_w/M_n$).

The PDI ($M_w/M_n$) of the BC non-woven preferably is low. It is known that at a relatively low PDI refers to a more stable material and pore structure. A PDI of nearly 1 would reflect a homogeneity which is nearly optimal. According to at least some embodiments, preferably the polydispersity index PDI ($M_w/M_n$) of the BC non-woven is less than 3.5, preferably less than 3.0, more preferably less than 2.75 and still more preferably less than 2.5, still more preferably less than 2.0, still more preferably less than 1.75, and most preferably less than 1.5.

According to at least some embodiments, preferably the BC non-woven is characterized by a degree of polymerization $DP_n$ of at least 1,000, more preferably at least 1,500, more preferably at least 1,700. Preferably, the article is characterized by a $DP_n$ of at most 8,000, more preferably at most 5,000, more preferably at most 3,000, still more preferably at most 2,500, still more preferably at most 2,200. A higher degree of polymerization will lead to increased tensile strength, whereas the $DP_n$ should not exceed the maximum.

The BC content of the BC non-woven preferably comprises carbonyl groups in an amount of less than 8.5 µmol/g, preferably of less than 8.0 µmol/g, more preferably of less than 7.5 µmol/g, still more preferably of less than 7.0 µmol/g, still more preferably of less than 6.0 µmol/g, and still more preferably of less than 5.75 µmol/g. The BC content of the BC non-woven preferably comprises carbonyl groups in an amount of at least 1.0 µmol/g, more preferably of at least 1.5 µmol/g, still more preferably of at least 2.0 µmol/g, still more preferably of at least 2.5 µmol/g, and most preferably of at least 2.75 µmol/g. A low amount of carbonyl groups corresponds to a higher degree of polymerization which will lead to increased tensile strength, whereas processability will be affected, if the amount of carbonyl groups is too high.

For cellulose, particularly, cellulose-containing articles, the crystallinity Ic is an important parameter. The degree of crystallinity is preferably determined by solid state NMR spectroscopy. A low crystallinity Ic may particularly be accompanied by a decrease in the permeability for gases and liquids. For the purpose of the present invention, particularly the inventive BC non-woven and its use, a relatively high crystallinity Ic is desired, in order to provide a relatively high permeability for gases and liquids. Preferably, the crystallinity Ic of the BC of the BC non-woven is at least 55%, more preferably at least 60%, more preferably at least 65%, more preferably at least 70%, most preferably at least 80%. Preferably, crystallinity Ic of the BC of the BC non-woven is at most 95%, more preferably at most 90%, more preferably at most 85%.

A person skilled in the art will recognize that BC may exist in several crystalline polymorphs. In particularly preferred embodiments of the present invention, BC simultaneously crystallizes in a one-chain triclinic structure Iα, and a two-chain modification Iβ. In such embodiments, both polymorphs are packed in a parallel chain arrangement, but of various ratios in a BC-containing non-woven, depending on the origin and method of manufacturing. Preferably, the BC of the inventive BC non-woven comprises cellulose Iα in an amount of at least 10%, preferably at least 20%, more preferably at least 30% by weight of the BC non-woven. Preferably, the BC of the inventive BC non-woven comprises cellulose Iα in an amount of at most 90%, preferably at most 70%, more preferably at most 50% by dry weight of the BC non-woven. Additionally or alternatively, the BC of the inventive BC non-woven preferably comprises cellulose Iβ in an amount of at least 1%, preferably at least 5%, more preferably at least 10% by weight. Preferably, the BC of the inventive BC non-woven comprises cellulose Iβ in an amount of at most 90%, preferably at most 80%, more preferably at most 70%, still more preferably at most 60%, still more preferably at most 50%, and most preferably at most 45% by dry weight. Preferably, the amount of cellulose Iα and Iβ is determined on the basis of CP/MAS 13C NMR. The above ranges are preferable to achieve the desired properties of the BC non-woven.

Particularly, the inventive BC non-woven may comprise cellulose Iα and cellulose Iβ in a mass ratio of at most 2.75, preferably at most 2.5, more preferably at most 2.4. Preferably, the inventive BC non-woven comprises cellulose Iα and cellulose Iβ in a mass ratio of at least 1.5, preferably at least 2.0, more preferably at least 2.25. The above ratios are preferable to achieve the desired properties of the BC non-woven.

According to the present invention, the BC may be used for providing fluid, particularly water, and optionally at least one active agent, to a treated area of skin. A preferable water absorption capacity (WAC) and/or a preferable water retention capacity (WRC) of the BC non-woven may allow for an increase in the desired effect of treatment. Particularly, the inventive BC non-woven may have a water absorption capacity (WAC) of at least 5,000%, more preferably at least 9,000%, more preferably at least 15,000%.

As described herein, the water absorption capacity is calculated by the following formula:

$$WAC = mass(wet)/mass(dry) * 100\%.$$

Preferably, the BC non-woven has a water absorption capacity (WAC) of at most 20,000%, more preferably at most 10,000%, and still more preferably at most 8,000%. Optionally and preferably, the BC non-woven has a water absorption capacity (WAC) of from 2,000% to 14,000%, more preferably of from 6,000% to 11,000%.

The water retention capacity (WRC) of the inventive BC non-woven may be of at least 500%, preferably at least 600%, more preferably at least 700%, most preferably at least 750%. The water retention capacity (WRC) of the inventive BC non-woven may be of at most 3,000%, preferably at most 2,000%, more preferably at most 1,000%, most preferably at most 950%. The water retention capacity (WRC) as used herein is the ratio of wet mass at maximum WAC and dry mass determined after centrifugation of the BC non-woven for 15 min at 5,000 rpm.

As described herein, the water retention capacity is calculated by the following formula:

$$WRC = (mass(wet) - mass(dry))/mass(dry) * 100\%.$$

As described above, the BC non-woven of the present invention is preferably characterized by a high degree of homogeneity. Particularly preferably, the BC non-woven of the invention has a very homogeneous network structure, in particular very homogeneous density of the network structure, and/or a particularly homogeneous surface structure. The homogeneous structures of the BC non-woven preferably contribute to the homogeneity of several physical and/or chemical properties of the BC non-woven. In particularly preferred embodiments, WAC and/or WRC of the BC non-woven are highly reproducible.

Preferably, the structure of the BC non-woven is so homogeneous that the standard deviation of the WAC is at most 15%, further preferred at most 10%, further preferred at most 7%, further preferred at most 5%, further preferred at most 4%, further preferred at most 3%, even further preferred at most 2%, particularly preferred at most 1% of the respective mean value of WAC, wherein mean value and standard deviation are determined from at most 25, preferably at most 20, further preferred at most 15, further preferred at most 10, further preferred at most 7, further preferred at most 6 independent measured values. Preferably, mean value and standard deviation are determined from at least 3 independent measured values, more preferably from at least 4 independent measured values, more preferably from at least 5 independent measured values. In preferred embodiments, mean value and standard deviation are determined from 5 independent measured values, more preferably from 6 independent measured values.

The independent measured values are obtained by cutting essentially equally sized samples of 2 cm×2 cm from a BC non-woven and determining the WAC value for each sample independently. The skilled person knows how to determine the mean and the standard deviation based on a group of measured values. The mean value is determined by dividing the sum of the individual measured values by the number of measured values. The standard deviation corresponds to the square root of the sum of the squared deviations of the individual measured values from the mean value of the measured values, wherein the sum is divided by the number of measured values minus one prior to square rooting.

Preferably, the structure of the BC non-woven is so homogeneous that the standard deviation of the WRC is at most 15%, further preferred at most 10%, further preferred at most 7%, further preferred at most 5%, further preferred at most 4%, further preferred at most 3%, even further preferred at most 2%, particularly preferred at most 1% of the respective mean value of WRC, wherein mean value and standard deviation are determined from at most 25, preferably at most 20, further preferred at most 15, further preferred at most 10, further preferred at most 7, further preferred at most 6 independent measured values. Preferably, mean value and standard deviation are determined from at least 3 independent measured values, more preferably from at least 4 independent measured values, more preferably from at least 5 independent measured values. In preferred embodiments, mean value and standard deviation are determined from 5 independent measured values, more preferably from 6 independent measured values.

The independent measured values are obtained by cutting essentially equally sized samples of 2 cm×2 cm from a BC non-woven and determining the WRC value for each sample independently. The skilled person knows how to determine the mean and the standard deviation based on a group of measured values. The mean value is determined by dividing the sum of the individual measured values by the number of measured values. The standard deviation corresponds to the square root of the sum of the squared deviations of the individual measured values from the mean value of the measured values, wherein the sum is divided by the number of measured values minus one prior to square rooting.

Preferably, the structure of the BC non-woven is so homogeneous that the standard deviation of both WAC and WRC is at most 15%, further preferred at most 10%, further preferred at most 7%, further preferred at most 5%, further preferred at most 4%, further preferred at most 3%, even further preferred at most 2%, particularly preferred at most 1% of the corresponding mean value of WAC or WRC, respectively, wherein mean value and standard deviation are determined from at most 25, preferably at most 20, further preferred at most 15, further preferred at most 10, further preferred at most 7, further preferred at most 6 independent measured values. Preferably, mean value and standard deviation are determined from at least 3 independent measured values, more preferably from at least 4 independent measured values, more preferably from at least 5 independent measured values. In preferred embodiments, mean value and standard deviation are determined from 5 independent measured values, more preferably from 6 independent measured values.

The independent measured values are obtained by cutting essentially equally sized samples of 2 cm×2 cm from a BC non-woven and determining the WAC and WRC values for each sample independently. The skilled person knows how to determine the mean and the standard deviation based on a group of measured values. The mean value is determined by dividing the sum of the individual measured values by the number of measured values. The standard deviation corresponds to the square root of the sum of the squared deviations of the individual measured values from the mean value of the measured values, wherein the sum is divided by the number of measured values minus one prior to square rooting.

In particular for cosmetic, dermatological, medical and pharmaceutical use of the BC non-woven, it is advantageous if the BC non-woven adapts to the skin area to be treated, particularly to the geometry and dimensions of the limps or face. In particular for these properties, the tensile strength of the BC non-woven is of importance. Particularly, a too low tensile strength will not allow that the BC non-woven is flexible and thus will not allow that the BC non-woven adapts to the unevenness of the skin, particularly the unevenness of the face without the risk of tearing. The tensile strength of the inventive BC non-woven preferably is more than 100 MPa, more preferably more than 252 MPa, more preferably more than 275 MPa, more preferable more than 300 MPa, and most preferably more than 310 MPa. The tensile strength of the inventive BC non-woven preferably is less than 1,000 MPa, preferably less than 750 MPa, more preferably less than 500 MPa, and most preferably of less than 400 MPa. The tensile strength as referred to herein preferably is determined after hot pressing of the BC non-woven using a TIRAtest 2710 universal measuring device with a nominal force of 1.5 kN. Preferably, the tensile strength as referred to herein is determined according to DIN EN ISO 527-1:2012-06 and/or DIN EN ISO 527-2:2012-06.

The present application also relates to the use of the BC non-woven of the invention in dermatological, medical, pharmaceutical, diagnostic, nutritional, cosmetic, technical and protective equipment products. In accordance with the present application is in particular the use of the BC non-woven of the invention for dermatological applications, cosmetic applications, diagnostic applications (for example cell culture systems), technical applications (membranes) and for medical applications (for example wound coverings or skin implants).

The present invention also comprises an apparatus for producing BC non-woven. The apparatus comprises:
  A) At least one culture vessel,
  B) Means for adding fresh or recycled culture medium and/or removing consumed culture medium from the culture vessel,
  C) Means for removing produced BC non-woven from the culture vessel.

The apparatus of the present invention comprises at least one culture vessel according to feature A) described above. Preferably, the apparatus comprises exactly one culture vessel. In alternative embodiments, the apparatus comprises at least two, more preferably at least three culture vessels.

Preferably, the culture vessel has a synthesis area of at least 1 cm$^2$, more preferably at least 10 cm$^2$, more preferably at least 100 cm$^2$, more preferably at least 1,000 cm$^2$, more preferably at least 1 m$^2$ and still more preferably at least 10 m$^2$. Preferably, the culture vessel has a synthesis area of at most 50,000 m$^2$, more preferably at most 20,000 m$^2$, more preferably at most 1,000 m$^2$, still more preferably at most 100 m$^2$, still more preferably at most 50 m$^2$.

Preferably, the culture vessel has a substantially rectangular shape. Preferably, the aspect ratio of length to width of the culture vessel is at least 1.5. More preferably, the aspect ratio of length to width of the culture vessel is at least 2, more preferably at least 3, more preferably at least 5, more preferably at least 10, more preferably at least 15, more preferably at least 20, more preferably at least 25, more preferably at least 30, more preferably at least 50, more preferably at least 100. However, the respective aspect ratio should not be very high. Preferably, that the aspect ratio of length to width of the culture vessel is at most 10,000, more preferably at most 8,000, more preferably at most 5,000, more preferably at most 2,000, more preferably at most 1,000, more preferably at most 500. The inventors found that such aspect ratios are particularly advantageous for particularly efficient production of BC non-woven.

Preferably, the culture vessel has a length of at least 100 cm, more preferably at least 200 cm, more preferably at least 500 cm, more preferably at least 1,000 cm. Preferably, the culture vessel has a length of at most 1,000 m, more preferably at most 200 m, more preferably at most 100 m, more preferably at most 50 m, more preferably at most 20 m.

Preferably, the culture vessel has a width of at least 10 cm, more preferably at least 20 cm, more preferably at least 50 cm, more preferably at least 100 cm. Preferably, the culture vessel has a width of at most 100 m, more preferably at most 20 m, more preferably at most 10 m, more preferably at most 5 m, more preferably at most 2 m.

Preferably, the culture vessel has a temperature control system comprising a heating device and at least one temperature sensor in order to maintain and control the temperature of the culture medium. Preferably, the heating device provides heat to maintain the predetermined temperature that deviates by at most ±5 K, more preferably at most ±4 K, more preferably at most ±3 K, more preferably at most ±2 K, more preferably at most ±1 K, more preferably at most ±0.5 K, more preferably at most ±0.1 K, more preferably at most ±0.01 K within the culture medium.

According to feature B) described above, the apparatus comprises means for adding fresh or recycled culture medium and/or removing consumed culture medium from the culture vessel. Preferably, the means comprise one or more openings in the culture vessel that enable addition of fresh or recycled culture medium and/or removal of consumed culture medium from the culture vessel. The openings may comprise one or more top openings. Culture vessels with a central top opening are known from the prior art. However, the present inventors found that it may be advantageous for the production of BC if the means for adding fresh or recycled culture medium and/or removing consumed culture medium from the culture vessel are arranged on the bottom of the culture vessel because BC non-woven production may be significantly compromised if addition and/or removal of culture medium is done from the top of the culture vessel. In contrast, addition and/or removal of culture medium from the bottom of the culture vessel is not problematic. Hence, the means for adding fresh or recycled culture medium and/or removing consumed culture medium from the culture vessel are preferably arranged on the bottom of the culture vessel. The means may also be arranged on the side walls of the culture vessel. However, if the means are arranged on the side walls of the culture vessel, it is preferred that the means are arranged close to the bottom of the culture vessel so that addition and/or removal of culture medium can be done below the interface of BC and gaseous medium so that production of BC non-woven is not disturbed by addition and/or removal of culture medium. Preferably, the openings are sealable in order to prevent unintended leak out of culture medium from the culture vessel. Preferably, the openings are connectable to tubes and/or vessels in a sealable way that prevents unintended leak out of culture medium from the culture vessel during addition and/or removal of culture medium.

According to feature C) described above, the apparatus comprises means for removing produced BC non-woven from the culture vessel. The present inventors found that it is advantageous if the produced BC non-woven is removed from the culture vessel by pulling and/or pushing the BC non-woven out of the culture vessel in a direction substantially parallel to the interface of BC and gaseous atmosphere. This way of removal is advantageous for minimizing disturbance of the bacterial culture and for minimizing structural changes of the BC non-woven that might otherwise occur. In particular, structural changes of the BC network may be minimized or even avoided by this way of removal. Therefore, the means for removing produced BC non-woven from the culture vessel are preferably pulling and/or pushing means that enable exerting a force onto the BC non-woven that is directed substantially parallel to the interface of BC and gaseous atmosphere. In order to exert such a force, the pulling and/or pushing means are preferably contacting the BC non-woven directly or indirectly via contacting means such as hooks, slings or the like. Preferred pulling means are arranged essentially outside the culture vessel and extend into the culture vessel only with a minor part or via contacting means in order to contact the BC non-woven. Preferred pulling means are rolls, springs or the like. Pushing means are preferably located essentially inside the culture vessel. Preferred pushing means are rolls, band conveyors or the like. Preferably, the pulling and/or pushing means are connected to a control device for controlling the time and speed of BC removal.

Preferably, the apparatus comprises means for keeping the gaseous atmosphere above the culture medium at a predetermined temperature and/or relative humidity within a predetermined distance from the culture medium. Preferably, the apparatus comprises means for keeping the gaseous atmosphere above the culture medium at a predetermined temperature and/or relative humidity within a distance from the culture medium of up to 2 cm, more preferably up to 5 cm, more preferably up to 10 cm. Preferably, the predetermined temperature deviates from the temperature of the culture medium in the culture vessel by at most ±10 K, more preferably at most ±5 K, more preferably at most ±4 K, more preferably at most ±3 K, more preferably at most ±2 K, more preferably at most ±1 K, more preferably at most ±0.5 K, more preferably at most ±0.1 K. Preferably, the predetermined relative humidity is at least 70%, more preferably of at least 80%, more preferably of at least 85%, more preferably of at least 90%, more preferably at least 92%, more preferably at least 95%, more preferably at least 98%, more preferably at least 99%.

Preferably, the means for keeping the gaseous atmosphere above the culture medium at a predetermined temperature and/or relative humidity within a predetermined distance from the culture medium comprise a cover for covering the culture vessel. Preferably, the cover is configured to be detachably connected to the culture vessel in order to enable repeatable covering and uncovering of the culture vessel. In preferred embodiments, the cover is a lid. Preferably, the cover is transparent in order to enable online visual inspection of the production process without the need of removing the cover.

Alternatively or additionally, the cover may contain an isolation layer or an isolation layer may be placed on top of the cover in order to further improve maintaining the temperature and humidity of the air above the culture medium in the cultivation device.

Alternatively or additionally, the means for keeping the gaseous atmosphere above the culture medium at a predetermined temperature and/or relative humidity within a predetermined distance from the culture medium may comprise one or more heating means. The heating means may be electric heaters, gas heaters, convective, contact or radiant heaters or the like, or a combination of two or more of those.

Alternatively or additionally, the means for keeping the gaseous atmosphere above the culture medium at a predetermined temperature and/or relative humidity within a predetermined distance from the culture medium may comprise one or more humidifier, preferably in combination with a heating device in order to maintain the desired temperature of the humidified air.

Preferably, the apparatus comprises means for keeping the culture medium in the culture vessel at a predetermined temperature. Preferably, the predetermined temperature is from 20° C. to 40° C., more preferably from 25° C. to 33° C., more preferably from 28° C. to 30° C. Preferably, the means for keeping the culture medium in the culture vessel at a predetermined temperature comprise at least one heating device such as electric heaters, gas heaters, radiant heaters or the like, or a combination of two or more of those.

EXAMPLES

Example 1

Figure 1:
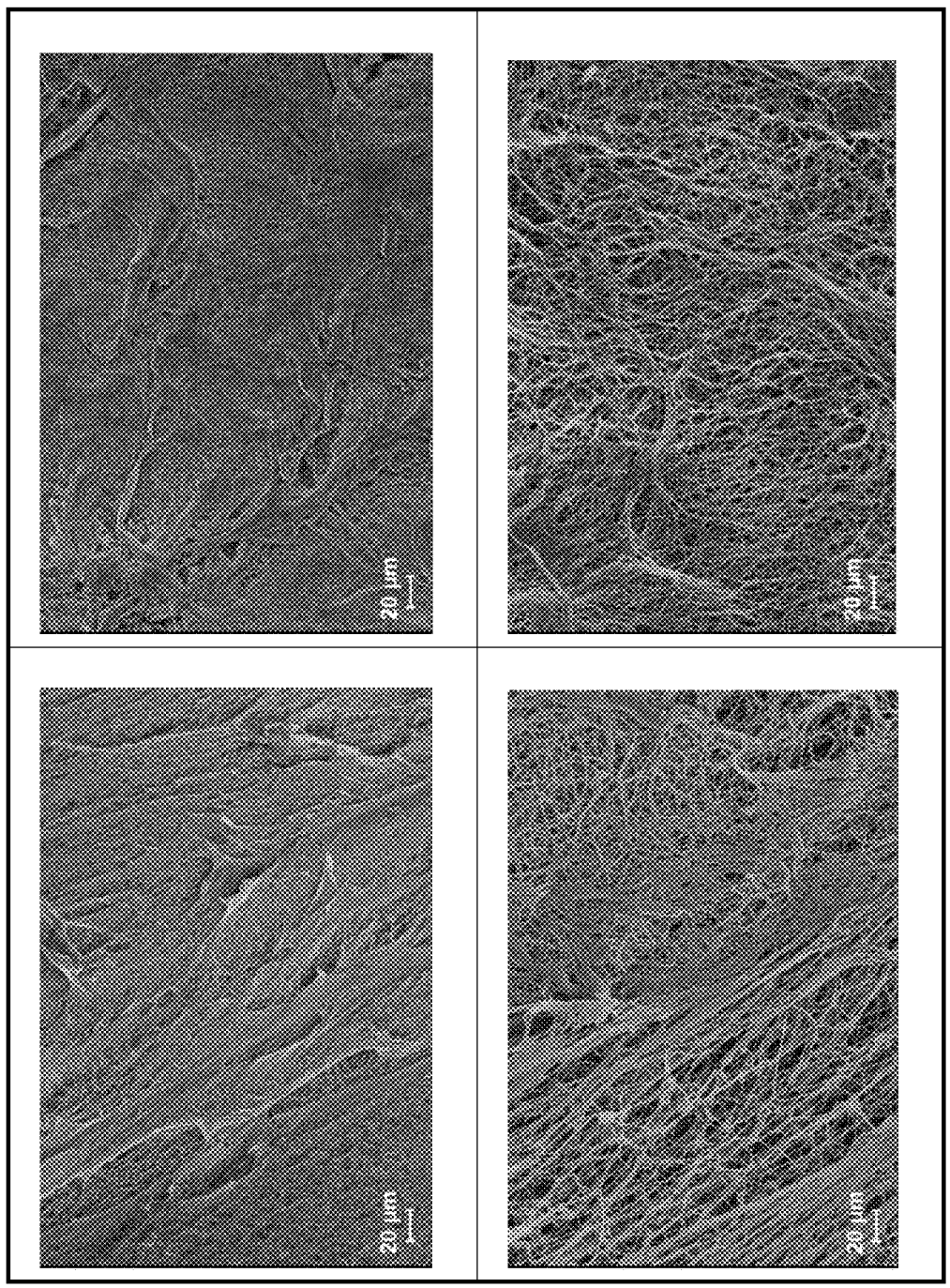
FIG. 1 shows scanning electron microscope images that allow comparison of cut edges obtained by fluid jet cutting (right panel) with cut edges obtained by cutting with a scalpel (left panel). The scanning electron microscope images show the cut edges with a magnification of 300× (upper panel) and 3000× (lower panel), respectively.
Figure 2:
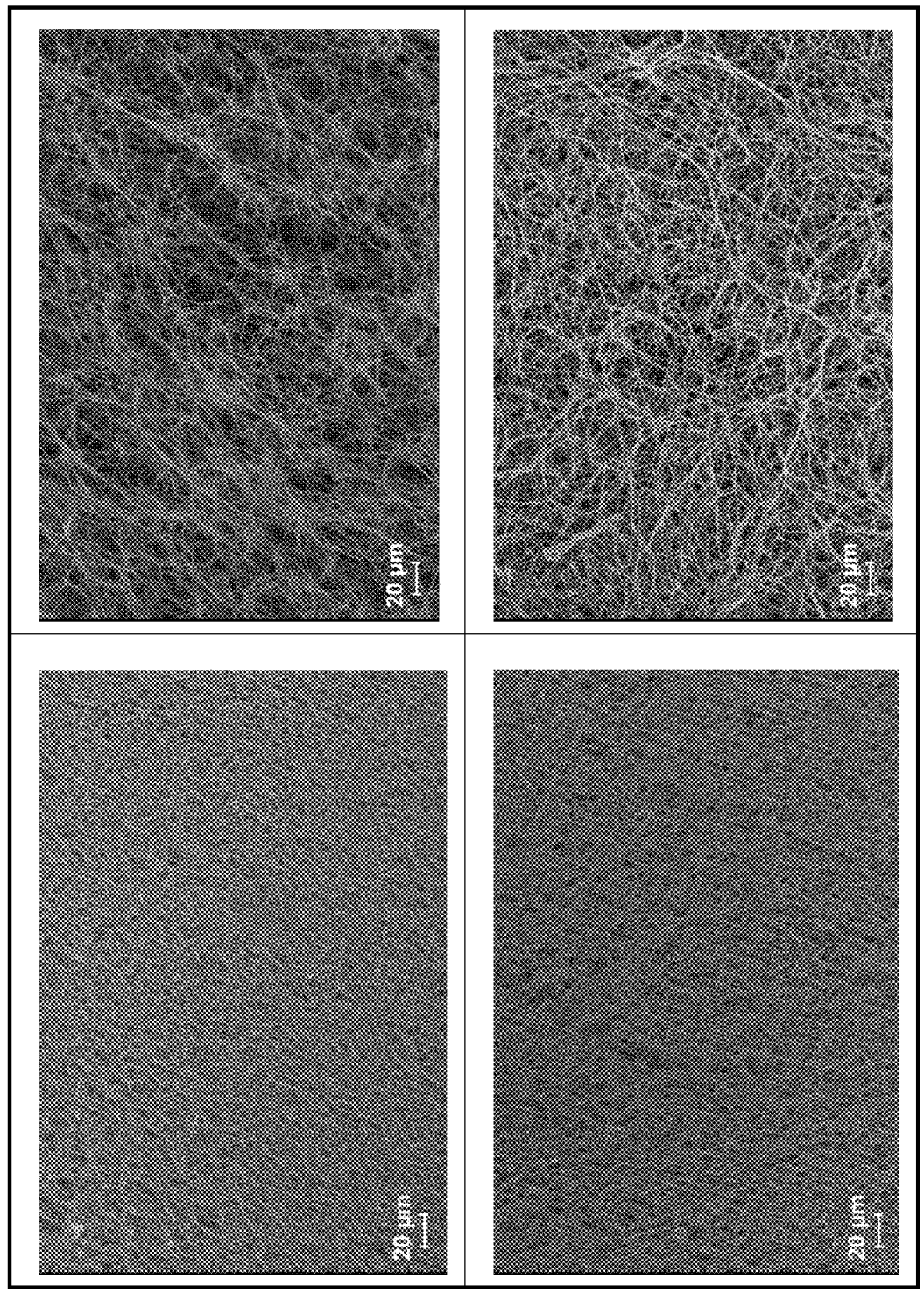
FIG. 2 shows scanning electron microscope images of BC non-woven sterilized with steam (upper panel) or e-beam (lower panel). The scanning electron microscope images show the BC with a magnification of 300× (left panel) and 3000× (right panel), respectively. Notably, the BC network structure is not compromised by e-beam sterilization in comparison to sterilization with steam.

BC non-woven was produced by the method of the present invention. Produced BC non-woven having an average thickness of 2 mm was removed from the culture vessel and separated from the BC non-woven that remained in the culture vessel. Separation was either done by cutting with a scalpel or by fluid jet cutting. The cut edges were investigated by scanning electron microscopy. It was found that the cut edges produced by fluid jet cutting were smoother as compared to the cut edges produced by cutting with a scalpel. The results are shown in FIG. 1.

Example 2

BC non-woven was produced by the method of the present invention. In particular, BC non-woven was sterilized with e-beam or by exposure to steam after removal from the culture vessel and separation from the BC that remained in the culture vessel. The BC network structure was investigated with scanning electron microscopy. It was found that the network structure was neither disturbed by sterilization with steam nor by e-beam sterilization.

Example 3

Three distinct BC non-woven materials were produced by the method of the present invention, which were characterized by a range of WAC and WRC values. Six samples of essentially equal size of 2 cm×2 cm were cut from each of the BC non-woven materials and WAC and WRC values were obtained independently for each of the six samples of each of the BC non-woven materials. For each sample, mean and standard deviation of WRC and WAC were calculated. Table 1 and 2 demonstrate the quality and homogeneity of the BC non-woven materials in view of standard deviations (SD) below ±5% for both characteristic material property values.

TABLE 1

Mean of water absorption capacity (in %) and corresponding standard deviations (in %) of different BC non-woven materials (n = 6 samples for each material)

| Material | Mean of WAC [%] | SD WAC [%] |
|---|---|---|
| Material 1 | 9,827 | 358 |
| Material 2 | 7,100 | 292 |
| Material 3 | 6,644 | 241 |

TABLE 2

Mean of water retention capacity (in %) and corresponding standard deviations (in %) of different BC non-woven materials (n = 6 samples for each material)

| Sample | Mean of WRC [%] | SD WRC [%] |
|---|---|---|
| Material 1 | 832 | 17 |
| Material 2 | 798 | 24 |
| Material 3 | 719 | 22 |

Example 4

The influence of covering the culture vessel with a lid on evaporation of water from the culture vessel was tested under laminar air flow conditions at a temperature of 28° C. The results are shown in table 3. It can be seen that covering the culture vessel with a lid reduced the amount of water that evaporated from the culture vessel by a factor of almost 50.

TABLE 3

Evaporation of water in L per $m^2$ culture vessel per day at T = 28° C. under laminar air flow conditions

| Test | Evaporation [L/($m^2$ · d)] |
|---|---|
| Test 1 (culture vessel without cover) | 4.9 |
| Test 2 (culture vessel with cover) | 0.1 |

Example 5

Two distinct BC non-woven materials were produced by the method of the present invention, which were characterized by a range of WAC and WRC values. The materials were produced under the conditions listed in table 4. In particular, the humidity of the gaseous atmosphere above the culture medium was kept at 79-80% and the temperature of the gaseous atmosphere 3 cm above the culture medium was kept at a temperature not more than 1 K below the temperature of the culture medium. The humidity and the temperature of the gaseous atmosphere at a distance from 0 to 2 cm measured perpendicular to the interface was not lower than the listed values in table 4. The samples of essentially equal size of 2 cm×2 cm were cut from each of the BC non-woven materials and WAC and WRC values were obtained independently for each of the samples of each of the BC non-woven materials. For each material, mean and standard deviation of WRC and WAC were calculated. Table 5 demonstrates the quality and homogeneity of the BC non-woven materials in view of standard deviations (SD) below ±5% for both characteristic material property values. Materials 4 and 5 show a smooth and even surface.

TABLE 4

Experimental conditions to obtain material 4 and 5

| Material | $\varphi$ [%] | $T_{GA}$ [° C.] | $T_{CM}$ [° C.] | $h_{BC}$ [mm] | t [%] |
|---|---|---|---|---|---|
| Material 4 | 79 | 28 | 29 | 4 | 100 |
| Material 5 | 80 | 28 | 29 | 4 | 100 |

($\varphi$ = relative humidity of the gaseous atmosphere above the bacterial culture, $T_{GA}$ = temperature of the gaseous atmosphere at a distance from the interface of BC and gaseous atmosphere of 3 cm measured perpendicular to the interface, $T_{CM}$ = temperature of the culture medium in the culture vessel, $h_{BC}$ = average thickness of the BC non-woven material, t = cultivation time relative to material 4)

TABLE 5

Mean and standard deviations of water absorption capacity and water retention capacity of BC non-woven material 4 (n = 10 samples) and BC non-woven material 5 (n = 6 samples)

| Material | Mean of WAC [%] | SD WAC [%] | Mean of WRC [%] | SD WRC [%] |
|---|---|---|---|---|
| Material 4 | 9,419 | 352 | 841 | 25 |
| Material 5 | 10,141 | 472 | 818 | 32 |

Example 6

Two distinct BC non-woven materials were produced as in example 5 with modifications of the experimental conditions to evaluate the influence of the humidity of the gaseous atmosphere. Namely, the gaseous atmosphere above the culture medium was kept at 31-33% and the cultivation time was extended to 225% relative to material 4. Table 6 demonstrates the insufficient quality and poor homogeneity of the BC non-woven materials in view of standard deviations (SD) above ±15% for water absorption and retention capacity as well as varying thickness between 2 two 6-7 mm. Material 6 and material 7 show an uneven surface.

TABLE 6

Experimental conditions to obtain material 6 and 7

| Material | $\varphi$ [%] | $T_{GA}$ [° C.] | $T_{CM}$ [° C.] | $h_{BC}$ [mm] | t [%] |
|---|---|---|---|---|---|
| Material 6 | 31 | 28 | 29 | 2-6 | 225 |
| Material 7 | 33 | 28 | 29 | 2-7 | 225 |

($\varphi$ = relative humidity of the gaseous atmosphere above the bacterial culture, $T_{GA}$ = temperature of the gaseous atmosphere at a distance from the interface of BC and gaseous atmosphere of 3 cm measured perpendicular to the interface, $T_{CM}$ = temperature of the culture medium in the culture vessel, $h_{BC}$ = average thickness of the BC non-woven material, t = cultivation time relative to material 4)

TABLE 7

Mean and standard deviations of water absorption capacity and water retention capacity of BC non-woven material 6 (n = 10 samples) and BC non-woven material 7 (n = 6 samples)

| Material | Mean of WAC [%] | SD WAC [%] | Mean of WRC [%] | SD WRC [%] |
|---|---|---|---|---|
| Material 6 | 10,298 | 2,087 | 802 | 141 |
| Material 7 | 9,633 | 1,914 | 838 | 149 |

The invention claimed is:

1. A method for producing bacterially synthesized cellulose (BC) non-woven, the method comprising the steps of:
   a) synthesizing BC by incubating a bacterial culture in a culture vessel, wherein the bacterial culture comprises a liquid culture medium and a BC-synthesizing bacteria,
   b) adding fresh or recycled culture medium and/or removing consumed culture medium during the incubation as an optional step,
   c) removing produced BC non-woven having an average thickness of at least 0.5 mm from the culture vessel,
   wherein at least during step a) the gaseous atmosphere above the bacterial culture is controlled to be at a temperature that is at most 10 K below the highest temperature of the culture medium in the culture vessel at all distances from the interface of BC and gaseous atmosphere within a range of from 0 to 2 cm measured perpendicular to the interface and/or wherein at least during step a) the gaseous atmosphere above the bacterial culture is controlled to be at a relative humidity of at least 70% at all distances from the interface of BC and gaseous atmosphere within a range of from 0 to 2 cm measured perpendicular to the interface.

2. The method according to claim 1, wherein synthesis of BC in the culture vessel continues during removal of produced BC non-woven having an average thickness of at least 0.5 mm from the culture vessel and wherein non-finished BC non-woven remains in the culture vessel and is separated from the BC non-woven that is removed, the method further comprising the following steps:
   d) continuing synthesis of BC in the culture vessel by continuation of incubation of the bacterial culture in the culture vessel,
   e) adding fresh or recycled culture medium and/or removing consumed culture medium during the continued incubation as an optional step,
   f) removing produced BC non-woven having an average thickness of at least 0.5 mm from the culture vessel, wherein synthesis of BC optionally continues during removal and
   wherein optionally non-finished BC non-woven remains in the culture vessel and is separated from the BC non-woven that is removed, and
   g) repeating steps d) to f) at least once as an optional step.

3. The method according to claim 1, wherein the temperature of the culture medium is from 20° C. to 40° C.

4. The method according to claim 1, wherein during step a) the gaseous atmosphere above the bacterial culture is controlled to be at a temperature that is at most 10 K below the temperature of the culture medium in the culture vessel and/or at a relative humidity of at least 70% at all distances from the interface of BC and gaseous atmosphere within a range of from 0 to 5 cm measured perpendicular to the interface.

5. The method according to claim 1, wherein the culture vessel is covered with a cover.

6. The method according to claim 1, wherein non-finished BC non-woven is separated from removed BC non-woven by fluid jet cutting.

7. The method according to claim 1, wherein the produced BC non-woven is removed from the culture vessel in step c) after at least three and at most ten days of incubation.

8. The method according to claim 2, wherein synthesis of BC in the culture vessel is continued in step d) by continuation of incubation of the bacterial culture in the culture vessel for at least 12 hours and at most 100 hours.

9. The method according to claim 1, wherein the method further comprises the step of sterilizing the BC non-woven by e-beam sterilization subsequent to step c).

10. The method according to claim 1, wherein the temperature of the culture medium is from 25° C. to 33° C.

11. The method according to claim 2, wherein during step d) the gaseous atmosphere above the bacterial culture is controlled to be at a temperature that is at most 10 K below the temperature of the culture medium in the culture vessel and/or at a relative humidity of at least 70% at all distances from the interface of BC and gaseous atmosphere within a range of from 0 to 5 cm measured perpendicular to the interface.

12. The method according to claim 4, wherein during step a) the gaseous atmosphere above the bacterial culture is controlled to be at a temperature that is at most 5 K below the temperature of the culture medium in the culture vessel and/or at a relative humidity of at least 95%.

13. The method according to claim 11, wherein during step d) the gaseous atmosphere above the bacterial culture is controlled to be at a temperature that is at most 5 K below the temperature of the culture medium in the culture vessel and/or at a relative humidity of at least 95%.

14. The method according to claim 2, wherein the method further comprises the step of sterilizing the BC non-woven by e-beam sterilization subsequent to step f).

15. The method according to claim 1, wherein at least during step a) the gaseous atmosphere above the bacterial culture is controlled to be at a relative humidity of at least 70% at all distances from the interface of BC and gaseous atmosphere within a range of from 0 to 2 cm measured perpendicular to the interface.

16. The method according to claim 1, wherein at least during step a) the gaseous atmosphere above the bacterial culture is controlled to be at a temperature that is at most 10 K below the highest temperature of the culture medium in the culture vessel at all distances from the interface of BC and gaseous atmosphere within a range of from 0 to 2 cm measured perpendicular to the interface and wherein at least during step a) the gaseous atmosphere above the bacterial culture is controlled to be at a relative humidity of at least 70% at all distances from the interface of BC and gaseous atmosphere within a range of from 0 to 2 cm measured perpendicular to the interface.

* * * * *